United States Patent
Morita et al.

(10) Patent No.: US 10,174,215 B2
(45) Date of Patent: Jan. 8, 2019

(54) INK, INK CARTRIDGE, INKJET RECORDING APPARATUS, PRINTED MATTER, PHOTOPOLYMERIZABLE COMPOUND, PHOTOCURABLE COMPOSITION, THREE-DIMENSIONAL OBJECT FORMATION MATERIAL, AND THREE-DIMENSIONAL OBJECT

(71) Applicants: Mitsunobu Morita, Shizuoka (JP); Soh Noguchi, Kanagawa (JP); Daisuke Miki, Kanagawa (JP)

(72) Inventors: Mitsunobu Morita, Shizuoka (JP); Soh Noguchi, Kanagawa (JP); Daisuke Miki, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/308,727

(22) PCT Filed: May 19, 2015

(86) PCT No.: PCT/JP2015/002502
§ 371 (c)(1),
(2) Date: Nov. 3, 2016

(87) PCT Pub. No.: WO2015/190037
PCT Pub. Date: Dec. 17, 2015

(65) Prior Publication Data
US 2017/0183519 A1 Jun. 29, 2017

(30) Foreign Application Priority Data

| | | |
|---|---|---|
| Jun. 10, 2014 | (JP) | 2014-119407 |
| Oct. 27, 2014 | (JP) | 2014-218124 |
| Mar. 6, 2015 | (JP) | 2015-044630 |

(51) Int. Cl.
| | |
|---|---|
| B33Y 70/00 | (2015.01) |
| B41J 2/175 | (2006.01) |
| C07C 69/54 | (2006.01) |
| C07C 69/96 | (2006.01) |
| C07C 271/12 | (2006.01) |
| C08F 222/10 | (2006.01) |
| C09D 11/101 | (2014.01) |
| C09D 11/107 | (2014.01) |
| C09D 11/322 | (2014.01) |
| C09D 11/324 | (2014.01) |
| C09D 11/38 | (2014.01) |
| C09D 135/02 | (2006.01) |

(52) U.S. Cl.
CPC .......... C09D 11/101 (2013.01); B33Y 70/00 (2014.12); B41J 2/17503 (2013.01); C07C 69/54 (2013.01); C07C 69/96 (2013.01); C07C 271/12 (2013.01); C09D 11/107 (2013.01); C09D 11/322 (2013.01); C09D 11/324 (2013.01); C09D 11/38 (2013.01); C09D 135/02 (2013.01); *C08F 2222/1013* (2013.01)

(58) Field of Classification Search
CPC ..... C09D 11/101; C09D 11/107; C09D 11/38; C09D 11/322; C09D 11/324; C09D 135/02; B33Y 70/00; B41J 2/17503; C07C 69/54; C07C 69/96; C07C 271/12; C08F 2222/1013
See application file for complete search history.

(56) References Cited

U.S. PATENT DOCUMENTS

| | | | |
|---|---|---|---|
| 5,921,779 A | 7/1999 | Podszun et al. | |
| 7,538,163 B2 * | 5/2009 | Bezuidenhout | C08G 18/10 525/455 |
| 2013/0144057 A1 | 6/2013 | Morita | |
| 2014/0120326 A1 | 5/2014 | Morita et al. | |
| 2014/0363634 A1 | 12/2014 | Morita et al. | |
| 2015/0042731 A1 | 2/2015 | Hiraoka | |

FOREIGN PATENT DOCUMENTS

| | | |
|---|---|---|
| EP | 2 602 244 A1 | 6/2013 |
| EP | 3 061 795 A1 | 8/2016 |
| JP | 57-014613 | 1/1982 |

(Continued)

OTHER PUBLICATIONS

Machine English translation of JP 2013-147462, Maki, Aug. 1, 2013.*
Machine English translation of JP 06-072955, Shiyoutaku et al., Mar. 15, 1994.*
International Search Report dated Aug. 25, 2015 for counterpart International Patent Application No. PCT/JP2015/002502 filed May 19, 2015.
Extended Search Report dated Mar. 10, 2017 in European Patent Application No. 15807470.8.
Maciej Podgórski, "Structure-property relationship in new photo-cured dimethacrylate-based dental resins", Dental Materials, 28, 2012, pp. 398-409.

(Continued)

*Primary Examiner* — Patrick D Niland
(74) *Attorney, Agent, or Firm* — Oblon, McClelland, Maier & Neustadt, L.L.P.

(57) ABSTRACT

Provided is an ink containing a compound represented by general formula (1) below where $R_1$ represents a hydrogen atom or a methyl group, n represents an integer of 2 or greater, a plurality of $R_1$ may be the same as or different from each other, X represents a hydrocarbon group having 2 to 10 carbon atoms, Y represents a tertiary hydroxyl group, or a group having an ester structure, and m represents an integer of 1 or greater.

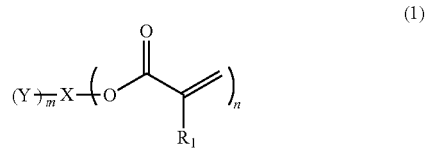

(1)

20 Claims, 1 Drawing Sheet

(56) References Cited

FOREIGN PATENT DOCUMENTS

| | | |
|---|---|---|
| JP | 62-265318 | 11/1987 |
| JP | 06-032761 | 2/1994 |
| JP | 06-072955 | 3/1994 |
| JP | 09-227324 | 9/1997 |
| JP | 2003-021900 | 1/2003 |
| JP | 2003-246818 | 9/2003 |
| JP | 2005-165246 | 6/2005 |
| JP | 2005-239848 | 9/2005 |
| JP | 2011-195724 | 10/2011 |
| JP | 2012-193292 | 10/2012 |
| JP | 5213395 | 3/2013 |
| JP | 2013-147462 | 8/2013 |
| JP | 2013-177517 | 9/2013 |
| JP | 2013-181114 | 9/2013 |
| JP | 2013-256487 | 12/2013 |
| RU | 2 373 242 C2 | 11/2009 |
| WO | WO 2013/069580 A1 | 5/2013 |

OTHER PUBLICATIONS

Combined Office Action and Search Report dated Jan. 31, 2018 in Russian Patent Application No. 2016148302 with English translation, 18 pages.

\* cited by examiner

[Fig. 1]
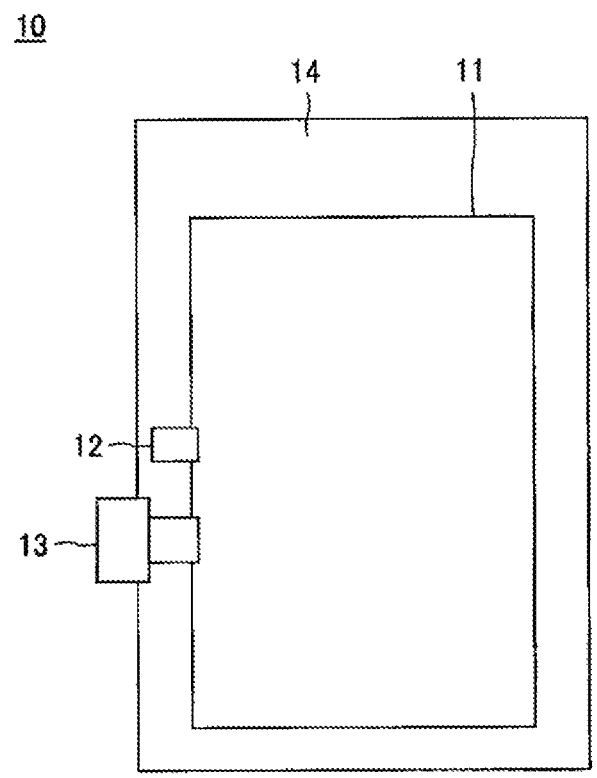
[Fig. 2]
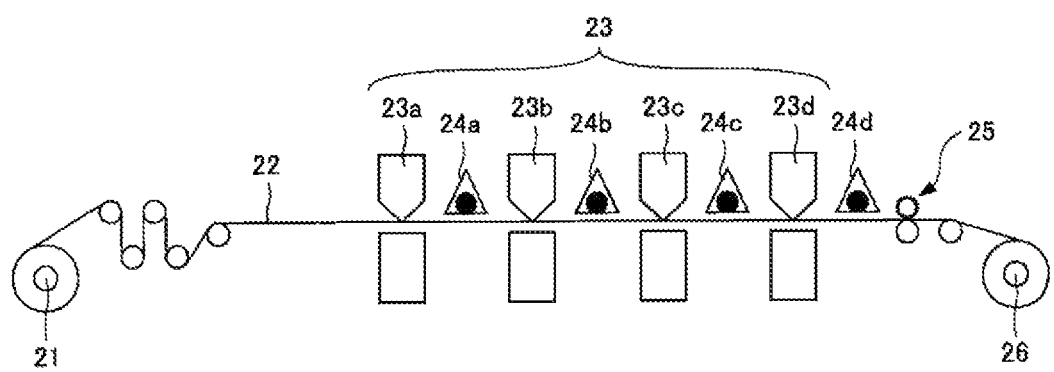

INK, INK CARTRIDGE, INKJET RECORDING APPARATUS, PRINTED MATTER, PHOTOPOLYMERIZABLE COMPOUND, PHOTOCURABLE COMPOSITION, THREE-DIMENSIONAL OBJECT FORMATION MATERIAL, AND THREE-DIMENSIONAL OBJECT

CROSS-REFERENCE TO RELATED APPLICATIONS

This application is a National Stage of PCT/JP2015/002502, which was filed on May 19, 2015. This application is based upon and claims the benefit of priority to Japanese Application No. 2014-119407, which was filed on Jun. 10, 2014, and to Japanese Application No. 2014-218124, which was filed on Oct. 27, 2014, and to Japanese Application No. 2015-044630, which was filed on Mar. 6, 2015.

TECHNICAL FIELD

The present invention relates to an ink, an ink cartridge, an inkjet recording apparatus, and printed matter using the ink, a photopolymerizable compound and a photocurable composition used in the ink, and a three-dimensional object formation material and a three-dimensional object made of the photocurable composition.

BACKGROUND ART

An inkjet recording method is known as a method for forming an image over a recording medium such as paper. This recording method has a high ink consumption efficiency, is excellent in resource saving, and can save ink costs per unit recording operation low.

In recent years, an inkjet recording method using an ultraviolet-curable ink has been gaining attention.

PTL 1 discloses a (meth)acrylate compound having a specific urethane structure, and an active energy ray-curable composition containing the compound, and an inkjet recording ink composition. PTLs 2 and 3 disclose an active energy ray-curable composition containing a (meth)acrylate compound of which mother nucleus is alkoxy group-modified hydrocarbon, and an inkjet recording ink composition. PTL 4 discloses a dental adhesive agent composition containing a glycerin di(meth)acrylate compound. PTL 5 discloses a side chain type polymerizable compound having an ether structure (—O—) or an ester structure (—COO—) on both of a main chain and a side chain of a molecule thereof, and a liquid crystal device using the same.

CITATION LIST

Patent Literature

PTL 1: Japanese Patent Application Laid-Open (JP-A) No. 2013-256487
PTL 2: JP-A No. 2003-246818
PTL 3: JP-A No. 2005-239848
PTL 4: JP-A No. 09-227324
PTL 5: JP-A No. 06-32761

SUMMARY OF INVENTION

Technical Problem

An object of the present invention is to provide an ink that uses a photopolymerizable compound having a lower viscosity and less odor than conventional ones, and is excellent in photopolymerizability and photocurability.

Solution to Problem

The object described above is achieved with the following invention 1).

1) An ink, containing a compound represented by general formula (1) below,

[Chem. 1]

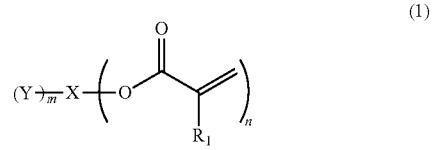

where in the formula above, $R_1$ represents a hydrogen atom or a methyl group, n represents an integer of 2 or greater, a plurality of $R_1$ may be the same as or different from each other, X represents a hydrocarbon group having 2 to 10 carbon atoms, Y represents a tertiary hydroxyl group, or a group having an ester structure, and m represents an integer of 1 or greater.

Advantageous Effects of Invention

The present invention can provide an ink that uses a photopolymerizable compound having a lower viscosity and less odor than conventional ones, and is excellent in photopolymerizability and photocurability.

BRIEF DESCRIPTION OF DRAWINGS

FIG. 1 is a diagram showing an example of an ink cartridge.
FIG. 2 is a diagram explaining a printing mechanism of an inkjet recording apparatus.

DESCRIPTION OF EMBODIMENTS (Ink)
A compound represented by general formula (1) below that is contained in an ink of the present invention contains: two or more (meth)acrylic acid ester structures as polymerizable functional groups; and one or more tertiary hydroxyl groups or one or more groups having an ester structure as a branch structure.

[Chem. 2]

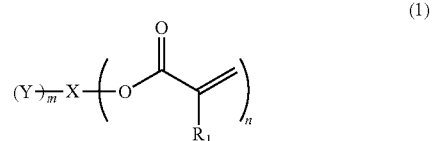

In the formula above, $R_1$ represents a hydrogen atom or a methyl group, n represents an integer of 2 or greater, a plurality of $R_1$ may be the same as or different from each other, X represents a hydrocarbon group having 2 to 10 carbon atoms, Y represents a tertiary hydroxyl group, or a group having an ester structure, and m represents an integer of 1 or greater.

The compound containing a plurality of (meth)acrylic acid ester structures, which are polymerizable functional groups, in a molecule thereof can form a cross-linked structure between the molecules thereof upon a polymerization reaction, and can be improved in curability. However, the molecular weight and viscosity of the compound will increase, as the number of (meth)acrylic acid ester structures in a molecule thereof increases, although curability thereof will be improved. Hence, it is preferable that n in the general formula (1) above be from 2 to 4, and more preferably 2 or 3.

Further, it is expected that incorporation of a polar structure in the molecules of a photopolymerizable compound (monomer) will enhance interactions between the molecules of the monomer and bring polymerizable functional groups thereof close to each other to thereby enhance polymerization reactivity of the monomer. However, for example, incorporation of a primary or secondary hydroxyl group (—OH) or a protic polar structure such as an amino group (—$NH_2$) in a monomer will increase the viscosity of the monomer, and cause troubles or limitations during use of the monomer as a photopolymerizable composition for various types of inks, etc. Furthermore, as the viscosity of a monomer increases, the mobility of the molecules of the monomer declines, which may inhibit the progress of a polymerization reaction of the monomer.

As compared with this, incorporation of a tertiary hydroxyl group or an aprotic polar structure in a monomer will result in lower intermolecular interactions than by incorporation of a protic polar structure as above, and will enable simultaneous satisfaction of suppression of viscosity thickening and enhancement of photopolymerization reactivity and photocurability. Particularly, incorporation of a group having an ester structure (an ester group or a carbonic acid ester) is considered to suppress viscosity thickening based on adequate flexibility of its linking portion linking to the mother nucleus structure and adequate intensity of the polarity of the ester structure, and enable simultaneous satisfaction of enhancement of photopolymerization reactivity and photocurability owing to the intermolecular interactions and viscosity suppression. However, also in this case, the viscosity of the monomer will increase as the number of aprotic polar structures increases, although the photopolymerization reactivity and photocurability of the monomer will be improved. Hence, it is preferable that m in the general formula (1) above be from 1 to 3, and more preferably 1 or 2.

Notwithstanding the above, incorporation of an ether structure, which is an aprotic polar structure likewise, is considered to be less capable of enhancing photopolymerization reactivity and photocurability of a monomer, because of resulting too low intermolecular interactions and a great freedom of the ether structure. Furthermore, incorporation of a urethane structure as an aprotic polar structure is considered to increase the viscosity of a monomer because of a stronger polar structure of the urethane structure than the ester structure, and stiffness of the urethane structure portion. Moreover, the same ester structure as above, which however is bonded reversely from the present invention (i.e., branched via a carbonyl carbon, not an oxygen atom), will incur viscosity thickening of a monomer, because such bonding deprives the ester bond portion of its freedom, leading to stiffness of the molecules.

As clarified from the above description, the compound represented by the general formula (1) above is excellent in photopolymerizability and photocurability because intermolecular interactions and a degree of molecular freedom thereof can be adjusted to a fine balance, and has less odor. Furthermore, the compound can be suppressed from viscosity thickening, and will have a low viscosity particularly when the polar group thereof is a group having an ester structure. Hence, the compound represented by the general formula (1) above is suitable for an ink.

In the compound represented by the general formula (1) above, X represents a hydrocarbon group having 2 to 10 carbon atoms. Specific examples thereof include the groups shown below. Note that X also encompasses those of which hydrocarbon chain is linked via a heteroatom.

[Chem. 3]

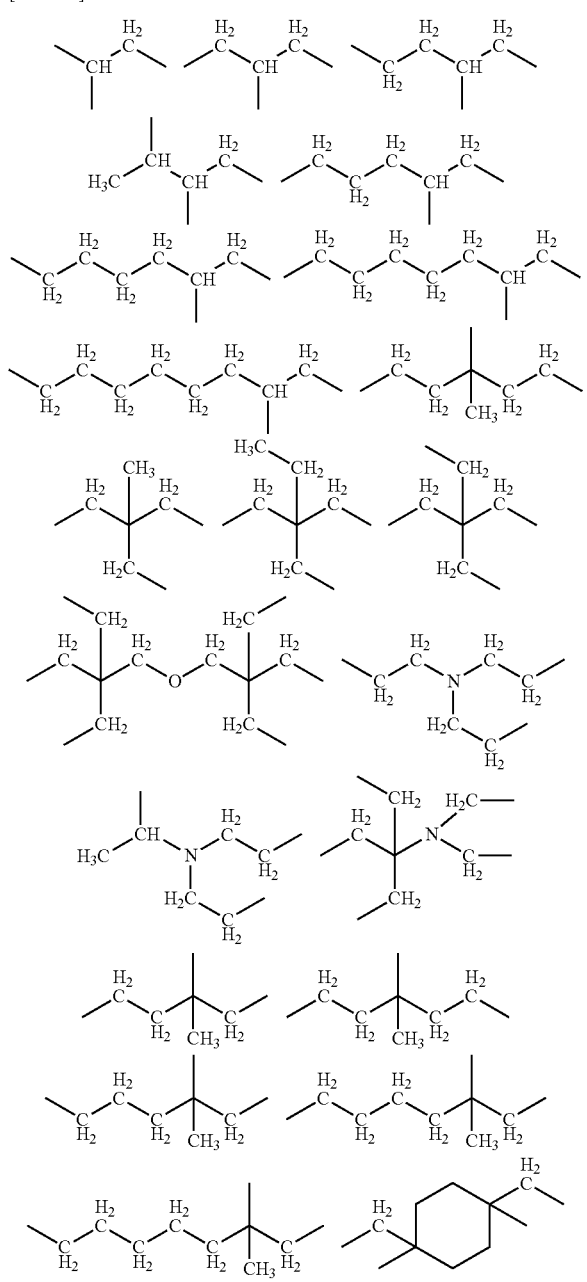

Among these, groups having 2 to 8 carbon atoms are preferable, and the groups shown below are particularly preferable.

[Chem. 4]

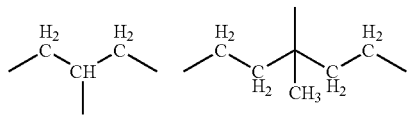

In the compound represented by the general formula (1) above, Y represents a tertiary hydroxyl group, or a group having an ester structure. A group represented by general formula (2) below, a group represented by general formula (3) below, or both thereof is/are preferable as the group having an ester structure. In the formula, $R_2$ is a hydrocarbon group having 1 to 15 carbon atoms, and preferably a hydrocarbon group having 1 to 10 carbon atoms. Specific examples of $R_2$ include a methyl group, an ethyl group, a propyl group, a butyl group, a pentyl group, a hexyl group, a heptyl group, an octyl group, a nonyl group, and a decyl group. These groups may be straight-chained, or may be branched. Among these, a methyl group, and an ethyl group are preferable.

[Chem. 5]

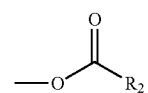
(2)

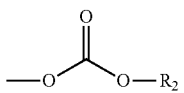
(3)

Next, specific examples of the photopolymerizable compound of the present invention will be shown below. However, the photopolymerizable compound of the present invention is not limited to those. Note that $R_1$ and $R_2$ in these examples are as described above.

[Chem. 6]

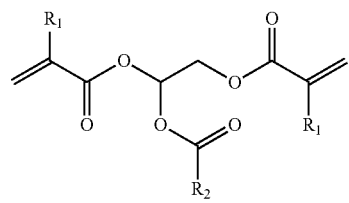

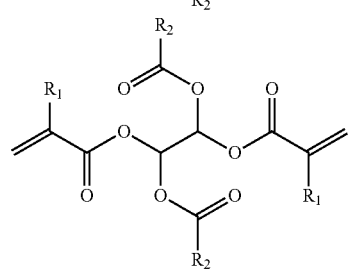

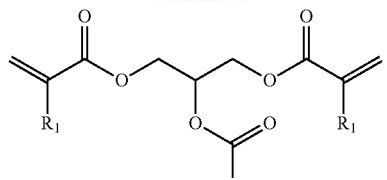

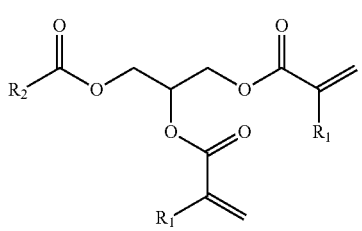

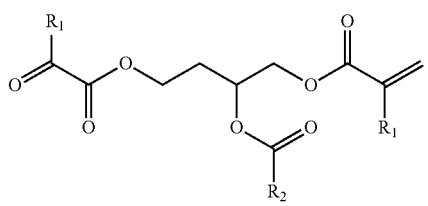

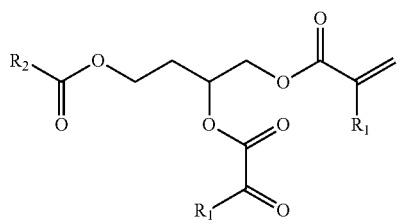

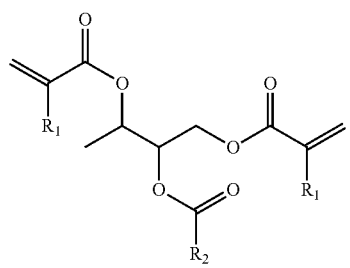

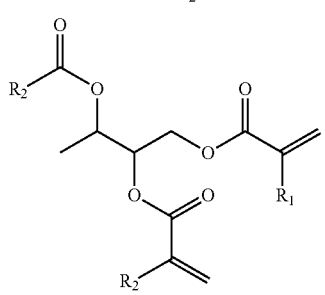

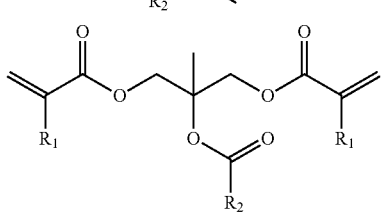

7
-continued
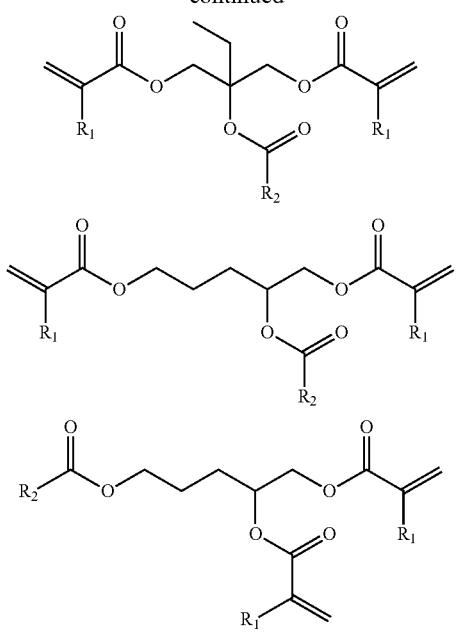
[Chem. 7]
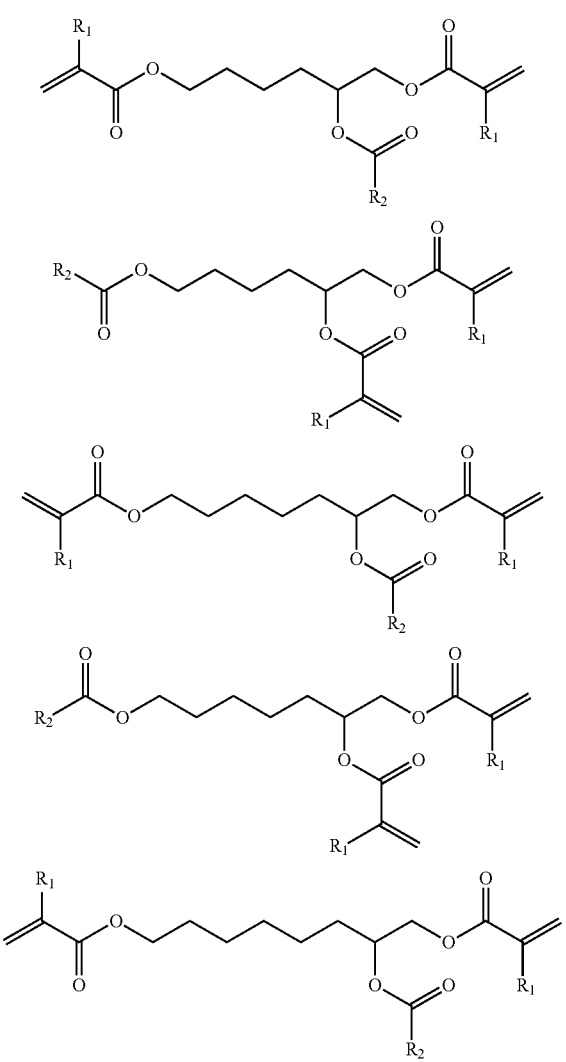
8
-continued
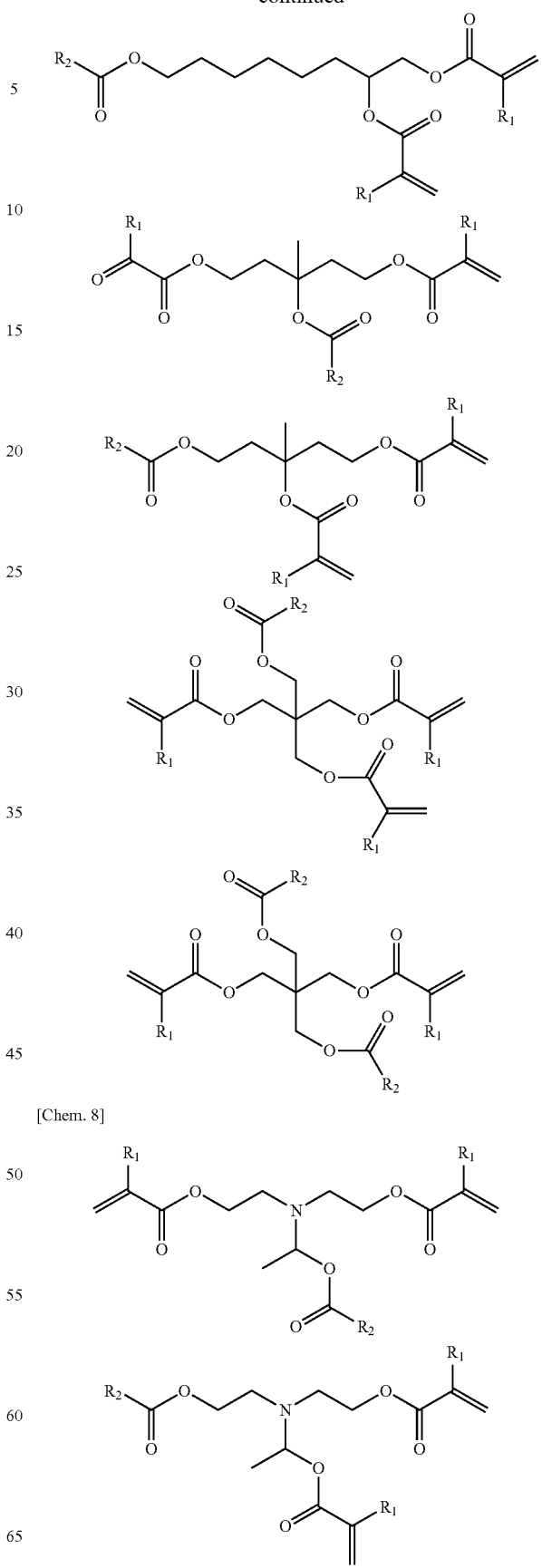
[Chem. 8]

-continued

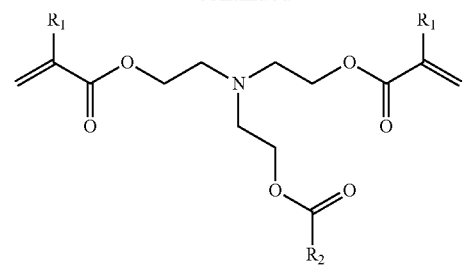

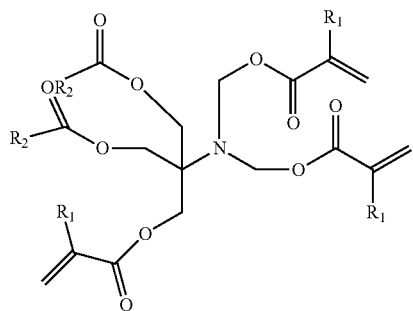

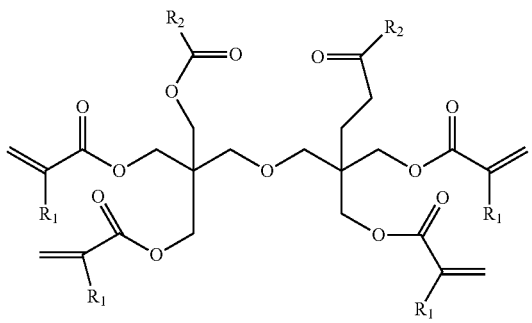

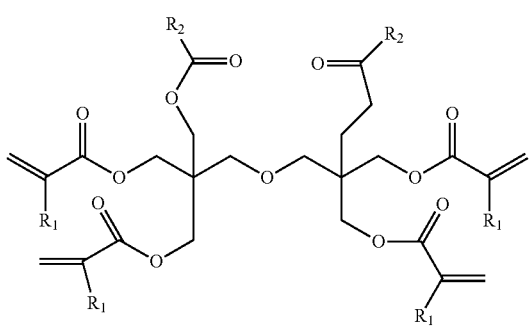

[Chem. 9]

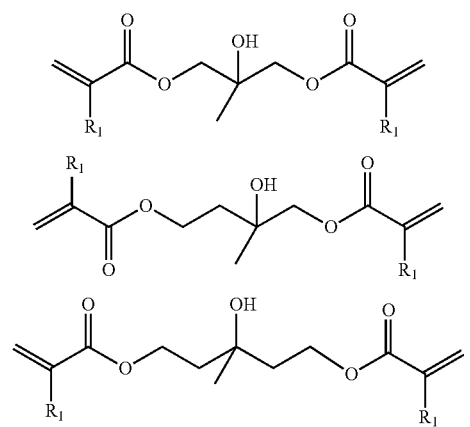

-continued

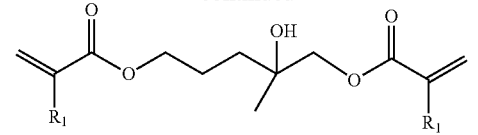

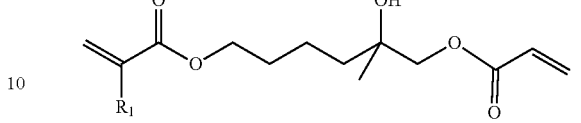

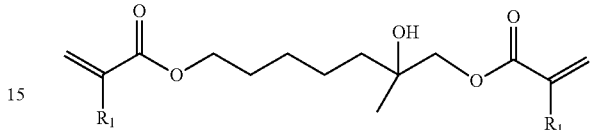

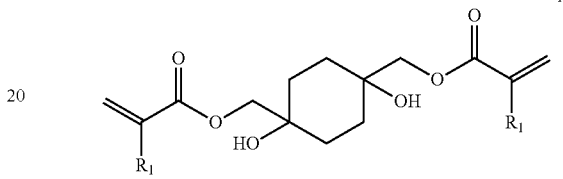

The photopolymerizable compound of the present invention may be a mixture of two or more different compounds. In this case, examples of the different compounds include structural isomers. The mixing ratio is not particularly limited.

A preferable range of the viscosity of the photopolymerizable compound of the present invention is different depending on the applications of the ink. Besides, there may be cases when a plurality of photopolymerizable compounds are used in combination. Therefore, a preferable viscosity range cannot be determined flatly. However, the viscosity thereof at 25° C. is typically about 50 mPa·s or lower, preferably 20 mPa·s or lower, and more preferably 15 mPa·s or lower.

The content of the photopolymerizable compound in the ink is typically from 20% by mass to 98% by mass, preferably from 30% by mass to 90% by mass, and more preferably from 30% by mass to 80% by mass.

It is preferable that the ink further contain a photopolymerization initiator.

Examples of the photopolymerization initiator include a photoradical polymerization initiator, a photocationic polymerization initiator (photoacid generator), and a photoanionic polymerization initiator (photobase generator). Two or more kinds may be used in combination. Among these, a photoradical polymerization initiator and a photoanionic polymerization initiator are preferable, and a photoradical polymerization initiator is particularly preferable.

A photopolymerization initiator is a compound that generates polymerization initiator species by absorbing an active energy ray.

An active energy ray is not particularly limited, and examples thereof include a γ ray, a β ray, an electron beam, an ultraviolet ray, visible light, and an infrared ray.

The photoradical polymerization initiator is not particularly limited, and examples thereof include aromatic ketones, an acyl phosphine oxide compound, an aromatic onium salt compound, an organic peroxide, a thio compound, a hexaaryl biimidazole compound, a ketoxime ester compound, a borate compound, an azinium compound, a metallocene compound, an active ester compound, a compound having a carbon-halogen bond, and an alkyl amine compound.

Specific examples of the photoradical polymerization initiator include benzophenone, Michler's ketone, 4,4'-bis(diethylamino)benzophenone, xanthone, thioxanthone, isopropyl xanthone, 2,4-diethyl thioxanthone, 2-ethyl anthraquinone, acetophenone, 2-hydroxy-2-methyl propiophenone, 2-hydroxy-2-methyl-4'-isopropyl propiophenone, 1-hydroxycyclohexyl phenylketone, isopropyl benzoin ether, isobutyl benzoin ether, 2,2-diethoxy acetophenone, 2,2-dimethoxy-2-phenyl acetophenone, camphorquinone, benzanthrone, 2-methyl-1-[4-(methylthio)phenyl]-2-morpholinopropan-1-one, ethyl 2-benzyl-2-dimethylamino-1-(4-morpholinophenyl)butanone-1,4-dimethylaminobenzoate, isoamyl 4-dimethylamino benzoate, 4,4'-di(t-butylperoxycarbonyl)benzophenone, 3,4,4'-tri(t-butylperoxycarbonyl)benzophenone, 3,3',4,4'-tetra(t-butylperoxycarbonyl)benzophenone, 3,3',4,4'-tetra(t-hexylperoxycarbonyl)benzophenone, 3,3'-di(methoxycarbonyl)-4,4'-bis(t-butylperoxycarbonyl)benzophenone, 3,4'-bis(methoxycarbonyl)-4,3'-bis(t-butylperoxycarbonyl)benzophenone, 4,4'-bis(methoxycarbonyl)-3,3'-bis(t-butylperoxycarbonyl)benzophenone, 1,2-octanedione, 1-[4-(phenylthio)phenyl]-2-(o-benzoyloxime), 2-(4'-methoxystyryl)-4,6-bis(trichloromethyl)-s-triazine, 2-(3',4'-dimethoxystyryl)-4,6-bis(trichloromethyl)-s-triazine, 2-(2',4'-dimethoxystyryl)-4,6-bis(trichloromethyl)-s-triazine, 2-(2'-methoxystyryl)-4,6-bis(trichloromethyl)-s-triazine, 2-(4'-pentyloxystyryl)-4,6-bis(trichloromethyl)-s-triazine, 4-[p-N,N-di(ethoxycarbonylmethyl)]-2,6-di(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyryl)benzoxazole, 2-(p-dimethylaminostyryl)benzothiazole, 2-mercaptobenzothiazole, 3,3'-carbonylbis(7-diethylaminocoumarin), 2-(o-chlorophenyl)-4,4,5,5'-tetraphenyl-1,2'-biimidazole, 2,2'-bis(2-chlorophenyl)-4,4',5,5'-tetrakis(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morpholinopropionyl)-9-n-dodecyl carbazole, 1-hydroxycyclohexylphenylketone, bis(η5-2,4-cyclopentadien-1-yl)-bis[2,6-difluoro-3-(1H-pyrrol-1-yl)phenyl]titanium, bis(2,4,6-trimethylbenzoyl)phenylphosphineoxide, and 2,4,6-trimethylbenzoyl diphenylphosphineoxide.

Among these, bis(2,4,6-trimethylbenzoyl)phenylphosphineoxide (IRGACURE 819), 2,4,6-trimethylbenzoyl diphenylphosphineoxide (DAROCUR TPO), 1-hydroxycyclohexylphenylketone (IRGACURE 184), 2-methyl-1-[4-(methylthio)phenyl]-2-morpholinopropan-1-one (IRGACURE 907), and 2-dimethylamino-2-(4-methylbenzyl)-1-(4-morpholin-4-ylphenyl)butan-1-one (IRGACURE 379) all manufactured by BASF Japan Ltd. are preferable because they have a high solubility to other components contained in the ink and can make the ink cured with a small amount of ultraviolet ray irradiation.

A mass ratio of the photopolymerization initiator relative to a total amount of the photopolymerizable compound and a colorant is typically from 0.01 to 0.50, preferably from 0.02 to 0.40, and more preferably from 0.05 to 0.30.

The ink may further contain a colorant, and can hence form a color image.

The colorant is not particularly limited, and examples thereof include a pigment, an oil-soluble dye, a water-soluble dye, and a dispersive dye. Two or more kinds may be used in combination. Among these, a pigment and an oil-soluble dye are preferable because they have an excellent weatherability and a rich color reproducibility, and a pigment is more preferable.

It is preferable that the colorant be a compound that does not function as a polymerization inhibitor, in order not to reduce sensitivity to an active energy ray for a photopolymerization reaction.

Examples of a red pigment or a magenta pigment as the pigment include: Pigment Red 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, and 257; Pigment Violet 3, 19, 23, 29, 30, 37, 50, and 88; and Pigment Orange 13, 16, 20, and 36.

Examples of a blue pigment or a cyan pigment as the pigment include Pigment Blue 1, 15, 15:1, 15:2, 15:3, 15:4, 15:6, 16, 17-1, 22, 27, 28, 29, 36, and 60.

Examples of a green pigment as the pigment include Pigment Green 7, 26, 36, and 50.

Examples of a yellow pigment as the pigment include Pigment Yellow 1, 3, 12, 13, 14, 17, 34, 35, 37, 55, 74, 81, 83, 93, 94, 95, 97, 108, 109, 137, 138, 139, 153, 154, 155, 157, 166, 167, 168, 180, and 193.

Examples of a black pigment as the pigment include Pigment Black 7, 28, and 26.

Examples of a white pigment as the pigment include Pigment White 6, 18, and 21.

Examples of a yellow oil-soluble dye include: an aryl or heteryl azo dye having phenol, naphthol, aniline, pyrazolone, pyrrolidone, or an open-chain active methylene compound as a coupling component; a methine dye having an open-chain active methylene compound as a coupling component, such as an azomethine dye, a benzylidene dye, and a monomethine oxonol dye; a quinone-based dye such as a naphthoquinone dye, and an anthraquinone dye; a quinophthalone dye; a nitro-nitroso dye; an acridine dye; and an acridinone dye.

Examples of a magenta oil-soluble dye include: an aryl or heteryl azo dye having phenol, naphthol, or aniline as a coupling component; a methine dye having pyrazolone or a pyrazolotriazole as a coupling component, such as an azomethine dye, an arylidene dye, a styryl dye, a merocyanine dye, and an oxonol dye; a carbonium dye such as a diphenylmethane dye, a triphenylmethane dye, and a xanthene dye; a quinone dye such as naphthoquinone, anthraquinone, and anthrapyridone; and a condensed polycyclic dye such as dioxazine.

Examples of a cyan oil-soluble dye include: an indoaniline dye; an indophenol dye; a polymethine dye having pyrrolotriazole as a coupling component, such as an azomethine dye, a cyanine dye, an oxonol dye, and a merocyanine dye; a carbonium dye such as a diphenylmethane dye, a triphenylmethane dye, and xanthene dye; a phthalocyanine dye; an anthraquinone dye; an aryl or heteryl azo dye having phenol, naphthol, or aniline as a coupling agent; and an indigo or thioindigo dye.

Specific examples of the oil-soluble dye include: C.I. solvent black 3, 7, 27, 29, and 34; C.I. solvent yellow 14, 16, 19, 29, 30, 56, 82, 93, and 162; C.I. solvent red 1, 3, 8, 18, 24, 27, 43, 49, 51, 72, 73, 109, 122, 132, and 218; C.I. solvent violet 3; C.I. solvent blue 2, 11, 25, 35, 38, 67, and 70: C.I. solvent green 3, and 7; and C.I. solvent orange 2.

Specific examples of the dispersive dye include: disperse yellow 5, 42, 54, 64, 79, 82, 83, 93, 99, 100, 119, 122, 124, 126, 160, 184:1, 186, 198, 199, 201, 204, 224, and 237; C.I. disperse orange 13, 29, 31:1, 33, 49, 54, 55, 66, 73, 118, 119, and 163; C.I. disperse red 54, 60, 72, 73, 86, 88, 91, 92, 93, 111, 126, 127, 134, 135, 143, 145, 152, 153, 154, 159, 164, 167:1, 177, 181, 204, 206, 207, 221, 239, 240, 258, 277, 278, 283, 311, 323, 343, 348, 356, and 362; C.I. disperse violet 33; C.I. disperse blue 56, 60, 73, 87, 113, 128, 143, 148, 154, 158, 165, 165:1, 165:2, 176, 183, 185, 197, 198, 201, 214, 224, 225, 257, 266, 267, 287, 354, 358, 365, and 368; and C.I. disperse green 6:1, and 9.

It is preferable that the pigment be dispersed adequately in the ink.

A disperser for dispersing the pigment is not particularly limited, and examples thereof include a ball mill, a sand mill, a ring mill, an attritor, a roll mill, an agitator, a Henschel mixer, a colloid mill, an ultrasonic homogenizer, a pearl mill, a wet jet mill, and a paint shaker.

A dispersant may be added for dispersing the pigment. The dispersant is not particularly limited, but a polymeric dispersant is preferable.

A mass ratio of the dispersant relative to the pigment is typically from 0.01 to 0.50.

An average particle diameter of the pigment in the ink is typically from 0.005 µm to 0.5 µm, preferably from 0.01 µm to 0.45 µm, and more preferably from 0.015 µm to 0.4 µm. This makes it possible to suppress clogging of head nozzles, and maintain storage stability, transparency, and photocurability of the ink.

The content of the colorant in the ink is typically from 0.5% by mass to 10% by mass, and preferably from 1% by mass to 8% by mass.

Note that the content of the colorant in a white ink that contains a white pigment such as titanium oxide as the colorant is typically from 5% by mass to 30% by mass, and preferably from 10% by mass to 25% by mass. This makes it possible to ensure a hiding power.

The ink may contain any other photopolymerizable compound than the compound represented by the general formula (1). A mass ratio of the any other photopolymerizable compound relative to the compound represented by the general formula (1) is typically from 0.01 to 100, and preferably from 0.1 to 50.

The any other photopolymerizable compound is not particularly limited, and examples thereof include a photoradically polymerizable compound, a photocationically polymerizable compound, and a photoanionically polymerizable compound. Two or more kinds may be used in combination.

The photoradically polymerizable compound is not particularly limited except that it should be a compound having one or more photoradically polymerizable ethylenic unsaturated groups, and encompasses a monomer, an oligomer, a polymer, etc. Examples thereof include: unsaturated carboxylic acid such as acrylic acid, methacrylic acid, itaconic acid, crotonic acid, isocrotonic acid, and maleic acid, salts thereof, and compounds derived from these; an anhydride having an ethylenic unsaturated group; acrylonitrile; styrene; unsaturated polyester; unsaturated polyether; unsaturated polyamide; and unsaturated urethane.

Specific examples of the photoradically polymerizable compound include: acrylic acid derivatives such as 2-hydroxyethyl acrylate, butoxyethyl acrylate, carbitol acrylate, cyclohexyl acrylate, tetrahydrofurfuryl acrylate, benzyl acrylate, bis(4-acryloxypolyethoxyphenyl)propane, neopentyl glycol diacrylate, ethoxylated neopentyl glycol diacrylate, propoxylated neopentyl glycol diacrylate, 1,6-hexanediol diacrylate, ethylene glycol diacrylate, diethylene glycol diacrylate, triethylene glycol diacrylate, tetraethylene glycol diacrylate, polyethylene glycol diacrylate, propylene glycol diacrylate, dipropylene glycol diacrylate, tripropylene glycol diacrylate, tetrapropylene glycol diacrylate, polypropylene glycol diacrylate, pentaerythritol triacrylate, pentaerythritol tetraacrylate, dipentaerythritol tetraacrylate, trimethylolpropane triacrylate, tetramethylolmethane tetraacrylate, oligoester acrylate, and epoxy acrylate; methacrylic acid derivatives such as methyl methacrylate, n-butyl methacrylate, allyl methacrylate, glycidyl methacrylate, benzyl methacrylate, dimethylaminomethyl methacrylate, 1,6-hexanediol dimethacrylate, ethylene glycol dimethacrylate, triethylene glycol dimethacrylate, polyethylene glycol dimethacrylate, polypropylene glycol dimethacrylate, trimethylolethane trimethacrylate, trimethylolpropane trimethacrylate, and 2,2-bis(4-methacryloxypolyethoxyphenyl)propane; acrylamide derivatives such as N-methylol acrylamide, diacetone acrylamide, 2-hydroxyethyl acrylamide, and acryloylmorpholine; allyl compound derivatives such as allyl glycidyl ether, diallyl phthalate, and triallyl trimellitate; di- or tri-vinyl ether compounds such as ethylene glycol divinyl ether, ethylene glycol monovinyl ether, diethylene glycol divinyl ether, triethylene glycol monovinyl ether, triethylene glycol divinyl ether, propylene glycol divinyl ether, dipropylene glycol divinyl ether, butanediol divinyl ether, hexanediol divinyl ether, cyclohexane dimethanol divinyl ether, hydroxyethyl monovinyl ether, hydroxynonyl monovinyl ether, and trimethylolpropane trivinyl ether; monovinyl ether compounds such as ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexane dimethanol monovinyl ether, n-propyl vinyl ether, isopropyl vinyl ether, isopropenyl ether-o-propylene carbonate, dodecyl vinyl ether, diethylene glycol monovinyl ether, and octadecyl vinyl ether; and 2-ethylhexyl diglycol acrylate, 2-hydroxy-3-phenoxypropyl acrylate, 2-hydroxybutyl acrylate, hydroxypivalic acid neopentyl glycol diacrylate, 2-acryloyloxyethyl phthalic acid, methoxypolyethylene glycol acrylate, tetramethylolmethane triacrylate, 2-acryloyloxyethyl-2-hydroxyethyl phthalic acid, dimethylol tricyclodecane diacrylate, ethoxylated phenyl acrylate, 2-acryloyloxyethyl succinic acid, nonylphenol ethyleneoxide adduct acrylate, modified glycerin triacrylate, bisphenol A diglycidyl ether acrylic acid adduct, modified bisphenol A diacrylate, phenoxypolyethylene glycol acrylate, 2-acryloyloxyethyl hexahydrophthalic acid, bisphenol A propyleneoxide adduct diacrylate, bisphenol A ethyleneoxide adduct diacrylate, dipentaerythritol hexaacrylate, pentaerythritol triacrylate, tolylene diisocyanato urethane prepolymer, lactone-modified flexible acrylate, butoxyethyl acrylate, propylene glycol diglycidyl ether acrylic acid adduct, pentaerythritol triacrylate, hexamethylene diisocyanato urethane prepolymer, 2-hydroxyethyl acrylate, methoxy dipropylene glycol acrylate, ditrimethylolpropane tetraacrylate, pentaerythritol triacrylate, hexamethylene diisocyanato urethane prepolymer, stearyl acrylate, isoamyl acrylate, isomyristyl acrylate, isostearyl acrylate, and lactone-modified acrylate.

Examples of combination of the photopolymerizable compound and the photopolymerization initiator include a combination of a photocationically polymerizable compound and a photocationic polymerization initiator, and a combination of a photoanionically polymerizable compound and a photoanionic polymerization initiator, in addition to a combination of a photoradically polymerizable compound and a photoradical polymerization initiator.

Examples of the photocationically polymerizable compound include an epoxy compound, a vinyl ether compound, and an oxetane compound.

Examples of the photocationic polymerization initiator include: $B(C_6F_5)_4^-$, $PF_6^-$, $AsF_6^-$, $SbF_6^-$, and $CF_3SO_3^-$ salts of aromatic onium compounds such as diazonium, ammonium, iodonium, sulfonium, and phosphonium; a sulfonated product that can generate a sulfonic acid; a halide that can generate hydrogen halide; and an iron allene complex.

Examples of the photoanionically polymerizable compound include an epoxy compound, a lactone compound, an acrylic compound, and a methacrylic compound. Among these, acrylic-based compounds and methacrylic-based compounds presented as examples of the photoradically polymerizable compound are preferable.

Examples of the photoanionic polymerization initiator include an o-nitrobenzyl carbamate derivative, an o-acyl oxyl derivative, and an o-carbamoyl oxime amidine derivative.

The ink may further contain a sensitizer in order to promote decomposition of the photopolymerization initiator by active energy ray irradiation.

A sensitizer absorbs an active energy ray and becomes an electron-excited state, and contacts the polymerization initiator in this state to thereby promote a chemical change (decomposition, or generation of a radical, an acid, or a base) of the polymerization initiator by such effects as electron migration, energy transfer, heat generation, etc.

A mass ratio of the sensitizer relative to the photopolymerization initiator is typically from $5 \times 10^{-3}$ to 200, and preferably from 0.02 to 50.

The sensitizer is not particularly limited, and a sensitizing dye that has an absorption wavelength in a wavelength range of from 350 nm to 450 nm. Examples thereof include: polynuclear aromatics (e.g., pyrene, perylene, and triphenylene); xanthenes (e.g., fluorescein, eosin, erythrosine, rhodamine B, and rose Bengal); cyanines (e.g., thiacarbocyanine, and oxacarbocyanine); merocyanines (e.g., merocyanine, and carbomerocyanine); thiazines (e.g., thionine, methylene blue, and toluidine blue); acridines (e.g., acridine orange, chloroflavin, and acriflavin); anthraquinones (e.g., anthraquinone); squaryliums (e.g., squarylium); and coumarins (e.g., 7-diethylamino-4-methylcoumarin).

The ink may further contain a cosensitizer.

A consensitizer serves to further enhance the sensitivity of the sensitizing dye to an active energy ray, and suppress polymerization inhibition of the photopolymerizable compound due to oxygen.

The cosensitizer is not particularly limited, and examples thereof include: amine-based compounds such as triethanol amine, p-dimethylamino benzoic acid ethyl ester, p-formyldimethyl aniline, and p-methylthiodimethyl aniline; thiol such as 2-mercaptobenzothiazole, 2-mercaptobenzooxazole, 2-mercaptobenzoimidazole, 2-mercapto-4(3H)-quinazoline, and β-mercaptonaphthalene; and sulfides.

The ink may further contain a polymerization initiator. This makes it possible to improve a storage property (storage stability) of the ink, and to prevent clogging of a head due to thermal polymerization for when jetting the ink by heating the ink and lowering the viscosity thereof.

The polymerization initiator is not particularly limited, and examples thereof include hydroquinone, benzoquinone, p-methoxyphenol, TEMPO, TEMPOL, and a cupferron complex of aluminium.

The content of the polymerization initiator in the ink is typically from 200 ppm to 20,000 ppm.

The viscosity of the ink is typically from 7 mPa·s to 30 mPa·s, and preferably from 7 mPa·s to 25 mPa·s in view of jettability from an inkjet recording apparatus.

It is preferable that the ink be free from a solvent because it is an active energy ray-curable ink. However, in order to have a better adhesiveness with a recording medium after cured, the ink may contain a solvent, as long as the curing speed, etc. of the ink are not influenced.

The solvent is not particularly limited, and examples thereof include an organic solvent, and water.

The content of the organic solvent in the ink is typically from 0.1% by mass to 5% by mass, and more preferably from 0.1% by mass to 3% by mass.

The ink may further contain a surfactant, a leveling additive, a matting agent, and a polyester-based resin, a polyurethane-based resin, a vinyl-based resin, an acrylic-based resin a rubber-based resin, or a wax for adjusting film properties.

The ink may further contain a stickiness imparting agent (tackifier) free of a polymerization inhibiting property, in order to enhance adhesiveness with polyolefin, PET, etc.

(Ink Cartridge)

The ink may be contained in a container, and can be used in the form of an ink cartridge. This eliminates the need to directly touch the ink in such operations as ink replacement, etc. and makes it possible to prevent contamination of hands and fingers and clothes. This also prevents mixing of foreign matters such as dusts into the ink. The container is not particularly limited, and examples thereof include an ink bag made of an air-impermeable aluminium laminate film or resin film.

FIG. 1 shows an example of an ink cartridge.

An ink bag 11 has an ink injection port 12 and an ink discharge port 13. The ink bag 11 is filled with an ink through the ink injection port 12, deaerated of residual air in the ink bag 11, and then hermetically sealed with the ink injection port 12 fusion-bonded. For use of the ink bag 11, the ink discharge port 13 is pierced with a needle provided on the body of an inkjet recording apparatus, and the ink is supplied into the inkjet recording apparatus. The ink discharge port 13 is made of a rubber material.

The ink bag 11 is contained in a cartridge case 14 made of plastic, and detachably attached into the inkjet recording apparatus in the form of an ink cartridge 10. The detachable configuration makes it possible to improve work efficiency of ink replenishment, replacement, etc.

(Inkjet Recording Apparatus)

An inkjet recording apparatus includes an ink cartridge, and a jet head configured to perform recording by jetting an ink.

A method for jetting an ink is not particularly limited, and examples thereof include a serial jetting method, and an on-demand method. Examples of the on-demand method include a piezo method, a thermal method, and an electrostatic method.

A printing mechanism of the inkjet recording apparatus will be described with reference to FIG. 2.

The reference numerals 23 denote printing units. The printing units 23a, 23b, 23c, and 23d for yellow, magenta, cyan, and black respectively jet inks onto a print target base material 22 fed from a print target base material feeding roll 21. Yellow, magenta, cyan, and black inks are jetted separately. After this, the inks are irradiated and cured with ultraviolet rays from light sources 24a, 24b, 24c, and 24d for photo-curing the inks, to thereby form a color image. After this, the print target base material 22 is conveyed to a process unit 25 and a printed matter take-up roll 26.

The printing units 23a, 23b, 23c, and 23d may be provided with a heating mechanism in order for the inks to be liquefied at the ink jetting portions.

There may be some times when the temperature of the base material becomes high, which are often the case when a printed area of a color printed immediately before is large, or when a conveying speed is high. Hence, according to necessity, a contact or contactless mechanism for cooling the base material to about room temperature may be provided.

The print target base material 22 is not particularly limited, and examples thereof include paper, film, metal, and composite materials of these. The print target base material 22 may have a sheet shape. It may be one-side printable or both-side printable. Furthermore, ultraviolet irradiation by the light sources 24a, 24b, and 24c may be weakened or skipped, and ultraviolet irradiation may be performed with the light source 24d after a plurality of colors are printed. This allows for energy saving and cost saving.

(Printed Matter)

Examples of a printed matter recorded with the ink of the present invention include not only ones that are printed over a smooth surface such as regular paper and resin film, but also ones that are printed over a print target surface having undulations, and ones that are printed over a print target surface made of various materials such as metal and ceramic.

The photopolymerizable compound and a photocurable composition of the present invention are suitable as a material of an ink, but can also be used for a molding resin, a paint, an adhesive, an insulating material, a release agent, a coating material, a sealing material, various types of resists, and various types of optical materials. Further, the photocurable composition of the present invention can be used as a three-dimensional object formation material, and, for example, can be used as a binder of powder particles used in a powder layer stacking method, which is one of three-dimensional object forming methods, or as a three-dimensional object formation material of a material jet method of forming a three-dimensional object by jetting a photocurable composition onto a predetermined region, curing it with an ultraviolet ray, and sequentially stacking up such cured products, or of an optical modeling method of forming a three-dimensional object by sequentially stacking up cured layers having a predetermined shape that are formed by emitting an ultraviolet ray to a storage pool of a photocurable composition. A three-dimensional object forming apparatus for when the photocurable composition of the present invention is used as a three-dimensional object formation material is not particularly limited, and may be a publicly-known apparatus.

EXAMPLES

The present invention will be described below in greater detail by presenting Examples and Comparative Examples. The present invention is not limited by these Examples. Note that "part" and "%" in Examples represent "part by mass" and "% by mass". A $^1$H-NMR spectrum was measured with $^1$H-NMR (500 MHz) (manufactured by JEOL Ltd.), and an IR spectrum was measured with FT-IR SPECTRUM GX (manufactured by Perkin Elmer Co., Ltd.).

Example 1a

A compound 1 was synthesized according to the procedure below.

1-(acryloyloxy)-3-(methacryloyloxy)-2-propanol (5.4 g) (24 mmol) manufactured by Tokyo Chemical Industry Co., Ltd. was added to dehydrated dichloromethane (100 mL), and after a flask was internally purged with an argon gas, triethyl amine (3.6 g) (36 mmol) was added thereto. Then, after they were cooled to about −10° C., acetic acid chloride (2.4 g) (30 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a yellow oily matter. Then, the yellow oily matter was refined by column chromatography in which the column was filled with WAKOGEL C300 (manufactured by Wako Pure Chemical Industries, Ltd.) (200 g) and hexane and ethyl acetate were used as eluates, to thereby obtain a colorless oily matter (1.8 g) of the compound 1 represented by the chemical formula below (yield: about 28%).

[Chem. 10]

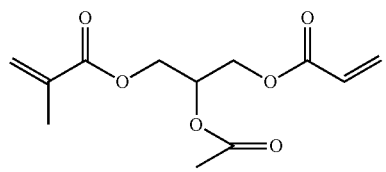

Identification data were as shown below.
$^1$H-NMR (CDCl$_3$): δ1.95 (s, 3H), 2.09 (d, 3H), 4.22-4.44 (m, 4H), 5.33-5.42 (m, 1H), 5.59-5.62 (m, 1H), 5.86-5.92 (m, 1H), 6.10-6.18 (m, 1H), 6.40-6.48 (m, 1H)
IR (NaCl): 2961, 1720, 1637, 1454, 1409, 1372, 1322, 1296, 1232, 1164, 1099, 1066, 1022, 985, 809, 602 cm$^{-1}$ Example 2a A compound 2 was synthesized according to the procedure below.

Glycerol dimethacrylate (5.7 g) (25 mmol) manufactured by Tokyo Chemical Industry Co., Ltd. was added to dehydrated dichloromethane (100 mL), and after a flask was internally purged with an argon gas, triethyl amine (3.6 g) (36 mmol) was added thereto. Then, after they were cooled to about −10° C., acetic acid chloride (2.4 g) (30 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a yellow oily matter. Then, the yellow oily matter was refined by column chromatography in which the column was filled with WAKOGEL C300 (manufactured by Wako Pure Chemical Industries, Ltd.) (200 g) and hexane and ethyl acetate were used as eluates, to thereby obtain a colorless oily matter (3.2 g) of the compound 2 represented by the chemical formula below (yield: about 47%).

[Chem. 11]

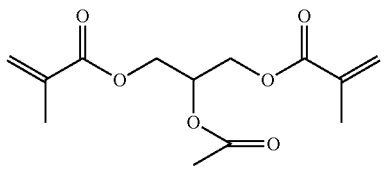

Identification data were as shown below.
$^1$H-NMR (CDCl$_3$): δ1.95 (s, 6H), 2.09 (d, 3H), 4.23-4.42 (m, 4H), 5.35-5.42 (m, 1H), 5.59-5.63 (m, 2H), 6.10-6.15 (m, 2H)

IR (NaCl): 2961, 1748, 1725, 1638, 1454, 1405, 1373, 1323, 1295, 1234, 1161, 1098, 1050, 1017, 946, 813, 651, 602 cm$^{-1}$

Example 3a

A compound 3 was synthesized according to the procedure below.

Glycerol dimethacrylate (13.7 g) (60 mmol) manufactured by Tokyo Chemical Industry Co., Ltd. was added to dehydrated dichloromethane (150 mL), and after a flask was internally purged with an argon gas, triethyl amine (7.9 g) (78 mmol) was added thereto. Then, after they were cooled to about −10° C., propionyl chloride (7.2 g) (78 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a brown oily matter. Then, the brown oily matter was refined by column chromatography in which the column was filled with WAKOGEL C300 (manufactured by Wako Pure Chemical Industries, Ltd.) (360 g) and hexane and ethyl acetate were used as eluates, to thereby obtain a colorless oily matter (7.1 g) of the compound 3 represented by the chemical formula below (yield: about 42%).

[Chem. 12]

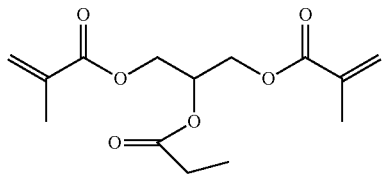

Identification data were as shown below.
$^{1}$H-NMR (CDCl$_3$): δ1.14 (t, 3H), 1.94 (s, 6H), 2.35 (q, 2H), 4.24-4.42 (m, 4H), 5.36-5.42 (m, 1H), 5.58-5.62 (m, 2H), 6.10-6.15 (m, 2H)
IR (NaCl): 2983, 2961, 1725, 1638, 1455, 1405, 1378, 1322, 1295, 1163, 1098, 1012, 945, 861, 813, 653 cm$^{-1}$ Example 4a A compound 4 was synthesized according to the procedure below.

Glycerol dimethacrylate (11.4 g) (50 mmol) manufactured by Tokyo Chemical Industry Co., Ltd. was added to dehydrated dichloromethane (100 mL), and after a flask was internally purged with an argon gas, triethyl amine (7.6 g) (75 mmol) was added thereto. Then, after they were cooled to about −10° C., butyryl chloride (6.9 g) (65 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a yellow oily matter. Then, the yellow oily matter was refined by column chromatography in which the column was filled with WAKOGEL C300 (manufactured by Wako Pure Chemical Industries, Ltd.) (300 g) and hexane and ethyl acetate were used as eluates, to thereby obtain a colorless oily matter (2.9 g) of the compound 4 represented by the chemical formula below (yield: about 19%).

[Chem. 13]

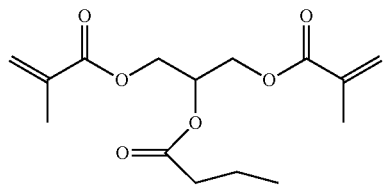

Identification data were as shown below.
$^{1}$H-NMR (CDCl$_3$): δ0.95 (t, 3H), 1.65 (q, 2H), 1.94 (s, 6H), 2.29-2.34 (m, 2H), 4.24-4.42 (m, 4H), 5.36-5.42 (m, 1H), 5.58-5.62 (m, 2H), 6.10-6.14 (m, 2H)
IR (NaCl): 2965, 2978, 1726, 1638, 1455, 1405, 1378, 1322, 1295, 1252, 1162, 1097, 1013, 945, 813, 652 cm$^{-1}$ Example 5a A compound 5 was synthesized according to the procedure below.

Glycerol dimethacrylate (9.1 g) (40 mmol) manufactured by Tokyo Chemical Industry Co., Ltd. was added to dehydrated dichloromethane (100 mL), and after a flask was internally purged with an argon gas, triethyl amine (6.1 g) (60 mmol) was added thereto. Then, after they were cooled to about −10° C., pivaloyl chloride (6.0 g) (50 mmol) was dropped thereto slowly such that the internal temperature of the system would be from −10° C. to −5° C., then they were stirred at room temperature for 2 hours, and then stirred at from 35° C. to 40° C. for 3 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a yellow oily matter. Then, the yellow oily matter was refined by column chromatography in which the column was filled with WAKOGEL C300 (manufactured by Wako Pure Chemical Industries, Ltd.) (300 g) and hexane and ethyl acetate were used as eluates, to thereby obtain a colorless oily matter (2.0 g) of the compound 5 represented by the chemical formula below (yield: about 16%).

[Chem. 14]

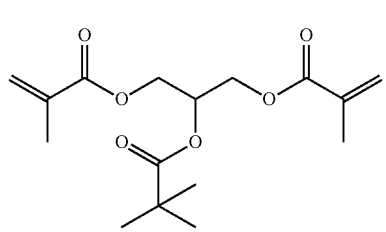

Identification data were as shown below.
$^{1}$H-NMR (CDCl$_3$): δ1.20 (s, 9H), 1.94 (s, 6H), 4.22-4.42 (m, 4H), 5.34-5.44 (m, 1H), 5.58-5.62 (m, 2H), 6.10-6.13 (m, 2H)

IR (NaCl): 2976, 2932, 1728, 1637, 1558, 1481, 1456, 1399, 1368, 1322, 1294, 1155, 1096, 1029, 1011, 943, 813, 768 cm$^{-1}$

Example 6a

A compound 6 was synthesized according to the procedure below.

Glycerol dimethacrylate (6.9 g) (30 mmol) manufactured by Tokyo Chemical Industry Co., Ltd. was added to dehydrated dichloromethane (100 mL), and after a flask was internally purged with an argon gas, triethyl amine (4.9 g) (48 mmol) was added thereto. Then, after they were cooled to about −10° C., 2-ethyl hexanoyl chloride (6.5 g) (40 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a colorless oily matter. Then, the colorless oily matter was refined by column chromatography in which the column was filled with WAKOGEL C300 (manufactured by Wako Pure Chemical Industries, Ltd.) (300 g) and hexane and ethyl acetate were used as eluates, to thereby obtain a colorless oily matter (3.5 g) of the compound 6 represented by the chemical formula below (yield: about 33%).

[Chem. 15]

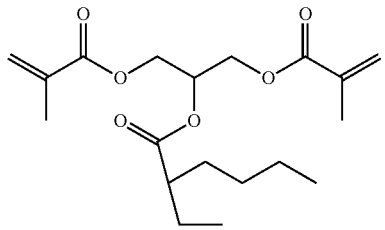

Identification data were as shown below.

$^1$H-NMR (CDCl$_3$): δ0.84-0.90 (m, 6H), 1.18-1.33 (m, 4H), 1.41-1.66 (m, 4H), 1.94 (s, 6H), 2.26-2.32 (m, 1H), 4.24-4.42 (m, 4H), 5.36-5.44 (m, 1H), 5.57-5.62 (m, 2H), 6.11-6.13 (m, 2H)

IR (NaCl): 2962, 2933, 2875, 1727, 1638, 1456, 1403, 1379, 1322, 1294, 1264, 1159, 1096, 1011, 943, 855, 813, 749, 652 cm$^{-1}$

Example 7a

A compound 7 was synthesized according to the procedure below.

Glycerol dimethacrylate (6.9 g) (30 mmol) manufactured by Tokyo Chemical Industry Co., Ltd. was added to dehydrated dichloromethane (100 mL), and after a flask was internally purged with an argon gas, triethyl amine (4.9 g) (48 mmol) was added thereto. Then, after they were cooled to about −10° C., lauroyl chloride (dodecanoyl chloride) (8.8 g) (40 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a colorless oily matter. Then, the colorless oily matter was refined by column chromatography in which the column was filled with WAKOGEL C300 (manufactured by Wako Pure Chemical Industries, Ltd.) (300 g) and hexane and ethyl acetate were used as eluates, to thereby obtain a colorless oily matter (1.5 g) of the compound 7 represented by the chemical formula below (yield: about 12%).

[Chem. 16]

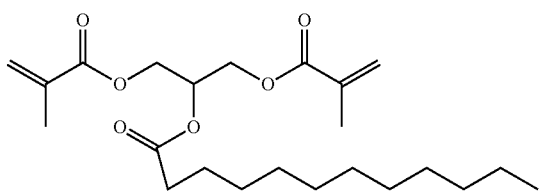

Identification data were as shown below.

$^1$H-NMR (CDCl$_3$): δ0.88 (t, 3H), 1.20-1.34 (m, 16H), 1.57-1.64 (m, 2H), 1.94 (s, 6H), 2.30-2.34 (m, 2H), 4.23-4.42 (m, 4H), 5.36-5.43 (m, 1H), 5.58-5.63 (m, 2H), 6.10-6.13 (m, 2H)

IR (NaCl): 2956, 2927, 2855, 1727, 1638, 1455, 1404, 1377, 1322, 1294, 1234, 1158, 1099, 1012, 942, 813, 722, 652 cm$^{-1}$

Example 8a

A compound 8 was synthesized according to the procedure below.

Glycerol dimethacrylate (13.7 g) (60 mmol) manufactured by Tokyo Chemical Industry Co., Ltd. was added to dehydrated dichloromethane (150 mL), and after a flask was internally purged with an argon gas, triethyl amine (7.9 g) (78 mmol) was added thereto. Then, after they were cooled to about −10° C., methyl chloroformate (7.4 g) (78 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a pale pink oily matter. Then, the pale pink oily matter was refined by column chromatography in which the column was filled with WAKOGEL C300 (manufactured by Wako Pure Chemical Industries, Ltd.) (390 g) and hexane and ethyl acetate were used as eluates, to thereby obtain a colorless oily matter (2.3 g) of the compound 8 represented by the chemical formula below (yield: about 13%).

[Chem. 17]

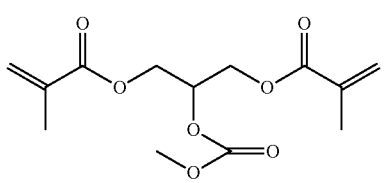

Identification data were as shown below.

$^1$H-NMR (CDCl$_3$): δ1.94 (s, 6H), 3.80 (d, 3H), 4.28-4.46 (m, 4H), 5.21-5.40 (m, 1H), 5.59-5.62 (m, 2H), 6.10-6.14 (m, 2H)

Example 9a

A compound 9 was synthesized according to the procedure below.

Glycerol dimethacrylate (13.7 g) (60 mmol) manufactured by Tokyo Chemical Industry Co., Ltd. was added to dehydrated dichloromethane (150 mL), and after a flask was internally purged with an argon gas, triethyl amine (7.9 g) (78 mmol) was added thereto. Then, after they were cooled to about −10° C., methyl chloroformate (8.5 g) (78 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a pale pink oily matter. Then, the pale pink oily matter was refined by column chromatography in which the column was filled with WAKOGEL C300 (manufactured by Wako Pure Chemical Industries, Ltd.) (380 g) and hexane and ethyl acetate were used as eluates, to thereby obtain a brown oily matter (5.2 g) of the compound 9 represented by the chemical formula below (yield: about 29%).

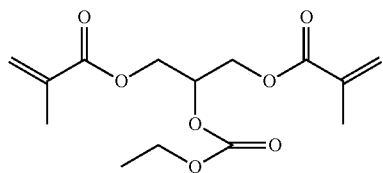

[Chem. 18]

Identification data were as shown below.

$^1$H-NMR (CDCl$_3$): δ1.32 (dd, 3H), 1.94 (s, 6H), 4.18-4.26 (m, 2H), 4.28-4.35 (m, 2H), 4.40-4.46 (m, 2H), 5.22-5.40 (m, 1H), 5.58-5.62 (m, 2H), 6.10-6.14 (m, 2H)

IR (NaCl): 2984, 2932, 1750, 1725, 1638, 1454, 1404, 1373, 1324, 1296, 1262, 1160, 1093, 1011, 945, 870, 813, 788, 653, 597 cm$^{-1}$

Example 10a

A compound 10 was synthesized according to the procedure below.

3-methylpentane-1,3,5-triol (6.7 g) (50 mmol) manufactured by Tokyo Chemical Industry Co., Ltd. was added to dehydrated dichloromethane (100 mL), and after a flask was internally purged with an argon gas, triethyl amine (12.1 g) (120 mmol) was added thereto. Then, after they were cooled to about −10° C., methacrylic acid chloride (10.5 g) (100 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a brown oily matter. Then, the brown oily matter was refined by column chromatography in which the column was filled with WAKOGEL C300 (manufactured by Wako Pure Chemical Industries, Ltd.) (350 g) and hexane and ethyl acetate were used as eluates, to thereby obtain a pale yellow oily matter (8.9 g) of the compound 10 represented by the chemical formula below (yield: about 66%).

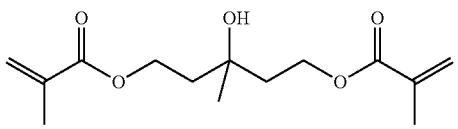

[Chem. 19]

Identification data were as shown below.

$^1$H-NMR (CDCl$_3$): δ1.30 (s, 3H), 1.91-1.95 (s+t, 6H+4H), 2.15 (br, 1H), 4.34 (t, 4H), 5.55-5.59 (m, 2H), 6.07-6.10 (m, 2H)

IR (NaCl): 3504, 2972, 1717, 1637, 1453, 1376, 1325, 1298, 1163, 1013, 943, 815 cm$^{-1}$

Example 11a

A compound 11 was synthesized according to the procedure below.

3-methylpentane-1,3,5-triol (13.4 g) (100 mmol) manufactured by Tokyo Chemical Industry Co., Ltd. was added to dehydrated dichloromethane (100 mL), and after a flask was internally purged with an argon gas, triethyl amine (24.3 g) (240 mmol) was added thereto. Then, after they were cooled to about −10° C., acrylic acid chloride (21.7 g) (240 mmol) was dropped thereto slowly such that the internal temperature of the system would be from −10° C. to −5° C., and then they were stirred at room temperature for 2 hours. Then, after a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a brown oily matter. Then, the brown oily matter was refined by column chromatography in which the column was filled with WAKOGEL C300 (manufactured by Wako Pure Chemical Industries, Ltd.) (350 g) and hexane and ethyl acetate were used as eluates, to thereby obtain a colorless oily matter (4.1 g) of the compound 11 represented by the chemical formula below (yield: about 17%).

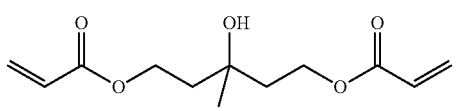

[Chem. 20]

Identification data were as shown below.

$^1$H-NMR (CDCl$_3$): δ1.30 (s, 3H), 1.88-1.98 (m, 5H), 4.36 (t, 4H), 5.84 (dd, 2H), 6.08-6.15 (m, 2H), 6.40 (dd, 2H)

IR (NaCl): 3491, 2972, 1724, 1636, 1619, 1463, 1410, 1298, 1277, 1199, 1057, 984, 812 cm$^{-1}$

Comparative Example 1a

Commercially available 1,6-hexanediol dimethacrylate represented by the chemical formula below was used as the compound of Comparative Example 1a.

[Chem. 21]

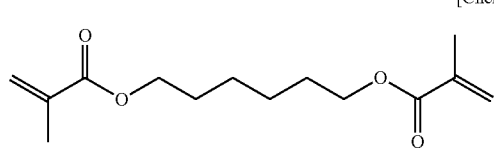

Comparative Example 2a

Commercially available 1,3-butanediol dimethacrylate represented by the chemical formula below was used as the compound of Comparative Example 2a.

[Chem. 22]

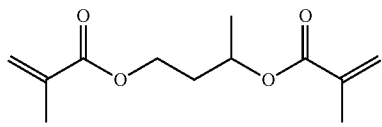

Comparative Example 3a

Commercially available neopentyl glycol dimethacrylate represented by the chemical formula below was used as the compound of Comparative Example 3a.

[Chem. 23]

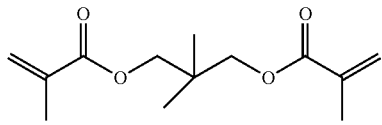

Comparative Example 4a

Commercially available diethylene glycol dimethacrylate represented by the chemical formula below was used as the compound of Comparative Example 4a.

[Chem. 24]

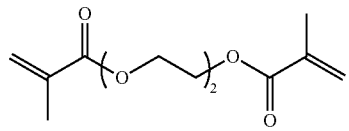

Comparative Example 5a

Commercially available polyethylene glycol dimethacrylate (p=9) represented by the chemical formula below was used as the compound of Comparative Example 5a.

[Chem. 25]

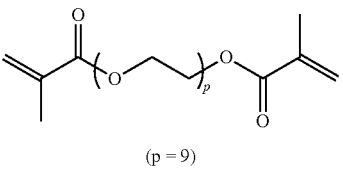

(p = 9)

Comparative Example 6a

Commercially available glycerol dimethacrylate represented by the chemical formula below was used as the compound of Comparative Example 6a.

[Chem. 26]

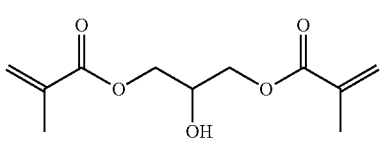

Comparative Example 7a

Commercially available 1-(acryloyloxy)-3-(methacryloyloxy)-2-propanol represented by the chemical formula below was used as the compound of Comparative Example 7a.

[Chem. 27]

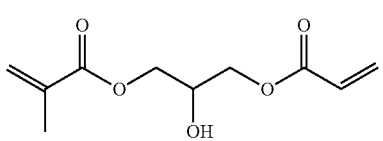

Comparative Example 8a

A comparative compound 1 was synthesized according to the procedure below.

Diethyl carbamoyl chloride (27.1 g, 200 mmol) was added slowly to a mixture of glycerin (46.0 g, 540 mmol) and pyridine (47 g) at room temperature, and then they were reacted at about 50° C. for about 15 hours. After the reaction mixture was concentrated at reduced pressure to remove excess pyridine, 10% hydrochloric acid was added thereto to acidify the reaction mixture, which was then concentrated at reduced pressure to remove water, to thereby obtain a brown oily matter. The obtained oily matter was extracted with ethyl acetate, and the extract layer was dried with anhydrous sodium sulfate. The ethyl acetate solution was concentrated, and a yellow oily matter (27 g) obtained as a result was refined by column chromatography (WAKOGEL C300, 400 g), to thereby obtain a colorless oily matter (16.1 g) represented by the chemical formula below as an intermediate product (yield: about 42%).

[Chem. 28]

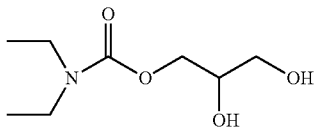

Identification data of the intermediate product were as shown below.

$^1$H-NMR (CDCl$_3$): δ1.13 (t, 6H), 3.23-3.33 (m, 4H), 3.56-3.62 (m, 1H), 3.63-3.69 (m, 1H), 3.73 (d, 1H), 3.77-3.82 (m, 1H), 3.86-3.92 (m, 1H), 4.20 (bs, 2H)

IR (NaCl): 3419, 2974, 2936, 2878, 1681, 1485, 1457, 1431, 1381, 1365, 1316, 1280, 1225, 1180, 1071, 1009, 770 cm$^{-1}$

Next, the intermediate product (6.7 g) (35 mmol) was added to dehydrated dichloromethane (70 mL), and after a flask was internally purged with an argon gas, triethyl amine (11.1 g) (110 mmol) was added thereto. After the mixture was cooled to about −10° C., methacrylic acid chloride (9.4 g) (90 mmol) was dropped thereto slowly such that the internal temperature of the system would be from −10° C. to −5° C., and then they were stirred at room temperature for 2 hours. A deposited product was removed by filtration, and the filtrate was washed with water, a saturated sodium bicarbonate aqueous solution, and a saturated sodium chloride aqueous solution, dried with sodium sulfate, and then concentrated at reduced pressure, to thereby obtain a brown oily matter. The obtained oily matter was refined by column chromatography (WAKOGEL C300, 250 g), to thereby obtain a colorless oily matter (7.8 g) of the comparative compound 1 represented by the chemical formula below (yield: about 68%).

[Chem. 29]

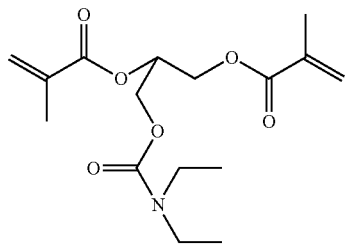

Identification data were as shown below.

$^1$H-NMR (CDCl$_3$): δ1.11 (bs, 6H), 1.94 (s, 6H), 3.25 (d, 4H), 4.25-4.45 (m, 4H), 5.44 (m, 1H), 5.60 (m, 2H), 6.12 (m, 2H)

IR (NaCl): 2977, 2933, 1724, 1706, 1638, 1479, 1456, 1428, 1379, 1319, 1294, 1274, 1226, 1164, 1097, 1074, 1013, 944, 854, 813, 767, 667 cm$^{-1}$

Comparative Example 9a

A comparative compound 2 was synthesized according to the procedure below.

Diethyl carbamoyl chloride (27.1 g) (200 mmol) was added slowly to a mixture of trimethylolpropane (67.0 g) (600 mmol) and pyridine (47 g) at room temperature, and then they were reacted at about 50° C. for about 15 hours. After the reaction mixture was concentrated at reduced pressure to remove excess pyridine, 10% hydrochloric acid was added thereto to acidify the reaction mixture, which was then concentrated at reduced pressure to remove water, to thereby obtain a brown oily matter. The obtained oily matter was extracted with ethyl acetate, and the extract layer was dried with anhydrous sodium sulfate. The ethyl acetate solution was concentrated, and a green oily matter (32 g) obtained as a result was refined by column chromatography (WAKOGEL C300, 400 g), to thereby obtain a colorless oily matter (17.7 g) represented by the chemical formula below as an intermediate product (yield: about 38%).

[Chem. 30]

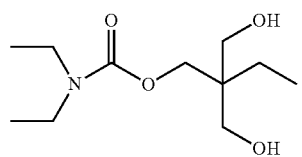

Identification data of the intermediate product were as shown below.

$^1$H-NMR (CDCl$_3$): δ0.89 (t, 3H), 1.14 (t, 6H), 1.28 (q, 2H), 3.23-3.34 (m, 4H), 3.48-3.59 (m, 4H), 3.62-3.66 (m, 2H), 4.23 (s, 2H)

IR (NaCl): 3431, 2970, 2935, 2881, 1678, 1487, 1459, 1431, 1380, 1316, 1279, 1225, 1180, 1069, 1004, 771 cm$^{-1}$

Next, the intermediate product (8.1 g) (35 mmol) was added to dehydrated dichloromethane (70 mL), and after a flask was internally purged with an argon gas, triethyl amine (11.1 g) (110 mmol) was added thereto. After the mixture was cooled to about −10° C., methacrylic acid chloride (11.1 g) (110 mmol) was dropped thereto slowly such that the internal temperature of the system would be from −10° C. to −5° C., and then they were stirred at room temperature for 2 hours. A deposited product was removed by filtration, and the filtrate was washed with water, a saturated sodium bicarbonate aqueous solution, and a saturated sodium chloride aqueous solution, dried with sodium sulfate, and then concentrated at reduced pressure, to thereby obtain a brown oily matter. The obtained oily matter was refined by column chromatography (WAKOGEL C300, 250 g), to thereby obtain a colorless oily matter (10.4 g) of the comparative compound 2 represented by the chemical formula below (yield: about 80%).

[Chem. 31]

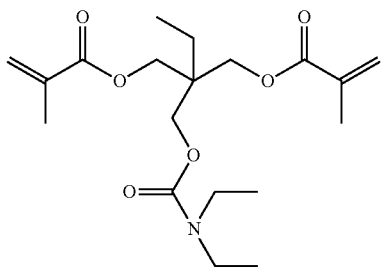

Identification data were as shown below.

$^1$H-NMR (CDCl$_3$): δ0.95 (t, 3H), 1.11 (t, 6H), 1.56 (q, 2H), 1.94 (s, 6H), 3.26 (d, 4H), 4.10 (s, 2H), 4.15 (s, 4H), 5.58 (m, 2H), 6.10 (bs, 2H)

IR (NaCl): 2974, 2933, 1722, 1705, 1636, 1558, 1540, 1473, 1457, 1428, 1379, 1321, 1294, 1273, 1226, 1162, 1073, 1014, 942, 813, 785, 768 cm$^{-1}$

Comparative Example 10a

A comparative compound 3 was synthesized according to the procedure below.

DL-tartaric acid (7.5 g) (50 mmol) manufactured by Tokyo Chemical Industry Co., Ltd. was dissolved in methanol (200 mL), HfCl$_4$ (THF)$_2$ (0.46 g) (1 mmol) was added thereto, and they were stirred at room temperature for 24 hours. The reaction mixture was filtered to remove insoluble matters, and the filtrate was concentrated at reduced pressure to thereby obtain a colorless oily matter (8.8 g) represented by the chemical formula below as an intermediate product (yield: about 99%).

[Chem. 32]

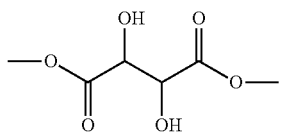

Identification data of the intermediate product were as shown below.

$^1$H-NMR (CDCl$_3$): δ3.50 (bs, 2H), 3.84 (s, 6H), 4.55 (s, 2H)

IR (NaCl): 3474, 2959, 1747, 1440, 1374, 1274, 1132, 1090, 1046, 1019, 979, 864, 826, 702, 605 cm$^{-1}$

Next, the intermediate product (3.6 g) (20 mmol) was added to dehydrated dichloromethane (100 mL), and after a flask was internally purged with an argon gas, triethyl amine (6.1 g) (60 mmol) was added thereto. After they were cooled to about −10° C., methacrylic acid chloride (5.0 g) (48 mmol) was dropped thereto slowly such that the internal temperature of the system would be from −10° C. to −5° C., and then they were stirred at room temperature for 2 hours. After a deposited product was removed by filtration, the filtrate was washed with water, a saturated sodium bicarbonate aqueous solution, and a saturated sodium chloride aqueous solution. Then, after the filtrate was dried with sodium sulfate, the resultant was concentrated at reduced pressure, to thereby obtain a reddish brown oily matter. The reddish brown oily matter was refined by column chromatography in which the column was filled with WAKOGEL C300 (manufactured by Wako Pure Chemical Industries, Ltd.) (250 g) and hexane and ethyl acetate were used as eluates, to thereby obtain a colorless oily matter (3.5 g) of the comparative compound 3 represented by the chemical formula below (yield: about 55%).

[Chem. 33]

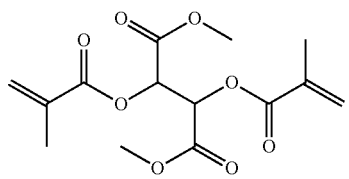

Identification data were as shown below.

$^1$H-NMR (CDCl$_3$): δ1.97 (s, 6H), 3.76 (s, 6H), 5.67-5.70 (m, 2H), 5.74 (s, 2H), 6.22-6.24 (m, 2H)

IR (NaCl): 2959, 2932, 2852, 1770, 1732, 1680, 1638, 1438, 1404, 1381, 1353, 1274, 1214, 1144, 1068, 1007, 950, 903, 854, 812, 706, 651 cm$^{-1}$

<Viscosity Measurement>

The viscosity of the compounds of Examples 1a to 11a and Comparative Examples 1a to 10a was measured with a viscoelasticity measuring instrument VAR200AD (manufactured by Reologica Instruments, Inc.) using a plate having a diameter of 40 mm at 25° C. The results are shown in Table 1.

<Odor Evaluation>

Odor of the compounds of Examples 1a to 11a and Comparative Examples 1a to 10a was evaluated according to the procedures (1) to (3) below. The evaluation criteria are as shown below. The results are shown in Table 1.

(1) Each compound (about 100 mg) (0.1 g) was weighed out in a 50 cc sample bottle (a glass bottle), and the sample bottle was capped.

(2) The sample bottle was left under room temperature conditions for about 30 minutes.

(3) Evaluator's nose was brought close to the sample bottle (glass bottle) to smell the odor when the cap was removed.

<Evaluation Criteria>

A: No odor was smelt, or odor was smelt but not uncomfortable.

B: A feeling of discomfort was aroused by a characteristic odor.

C: A strong feeling of discomfort was aroused by a characteristic odor.

Examples 1b to 11b and Comparative Examples 1b to 10b

<Production of Photocurable Composition>

Each of the compounds of Examples 1a to 11a and Comparative Examples 1a to 10a (950 mg), and a photopolymerization initiator IRGACURE 907 [2-methyl-1-[4-(methylthio)phenyl]-2-morpholinopropan-1-one] (manufactured by BASF Japan Ltd.) (50 mg) were mixed with a magnetic stirrer, to thereby produce photocurable compositions of Examples 1b to 11b and Comparative Examples 1b to 10b.

Photopolymerizability and photo-curability of the photocurable compositions of Examples 1b to 11b and Comparative Examples 1b to 10b were evaluated as described below. The results are shown in Table 1.

<Photopolymerizability>

Photopolymerizability of each photocurable composition was evaluated with a measuring instrument composed of DSC-7020 (manufactured by SII Inc.) and a spot light source LA-410UV (manufactured by Hayashi Watch-Works Co., Ltd.).

Specifically, an exothermic amount of the photopolymerizable compound when it was irradiated with an ultraviolet ray having a wavelength of 365 nm at 200 mW/cm$^2$ for a period of time enough for the photopolymerizable compound to complete the polymerization was measured twice for each sample. The exothermic amount obtained by the first measurement included an exothermic amount due to the ultraviolet irradiation, in addition to an exothermic amount due to the polymerization of the photopolymerizable compound. Hence, the sample that had completed the polymerization at the first measurement was irradiated with an ultraviolet ray again under the same conditions to measure an exothermic amount excluding an exothermic amount due to polymerization of the photopolymerizable compound. Then, an exothermic amount due to the polymerization of the photopolymerizable compound was calculated based on the difference between the first and second exothermic amounts. Here, a time T1 [s] taken from when the ultraviolet irradiation was started until when the maximum exothermic amount was reached was used as an index for comparison of the photopolymerization speed.

<Photo-Curability>

Photo-curability of each photocurable composition was measured with a measuring instrument composed of VAR200AD (manufactured by Reologica Instruments, Inc.) and an LED light source LIGHTNINGCURE LC-L1 (manufactured by Hamamatsu Photonics K.K.).

Specifically, a sample was inserted in a gap of 10 μm between cone and plate having a diameter of 20 mm, and then irradiated with an ultraviolet ray having a wavelength of 365 nm at 50 mW/cm$^2$, to measure changes of viscoelasticity until elastic modulus reached a saturated level. The maximum value of elastic modulus was determined from the measurement result and used as an indicator of a cured level.

Typically, an elastic modulus of $1\times10^4$ Pa indicates a sufficiently cured level. The photocurable compositions of all Examples and Comparative Examples had an elastic modulus of $1\times10^5$ Pa. This was because their elastic modulus was saturated substantially at $1\times10^5$ Pa, and elastic modulus measurement beyond that level was impossible. The result showed that all of the samples could form a hard state by being irradiated with sufficient light (by being given a lot of light energy). A sample of which elastic modulus reaches $1\times10^5$ Pa by a shorter period of time of light irradiation can be cured with lower energy and has a better photo-curability.

The energy of the ultraviolet ray irradiated until the elastic modulus reached a saturated level, i.e., a curing energy was calculated as a product between the intensity of the ultraviolet ray (50 mW/cm$^2$) and the period of time [s] for which the sample was irradiated with the ultraviolet ray.

TABLE 1

|  | Photopolymerizable compound | Viscosity (25° C.) (mPa·s) | Odor |  | Photopolymerizability T1 (s) | Photocurability Curing energy (mJ/cm$^2$) |
| --- | --- | --- | --- | --- | --- | --- |
| Ex. 1a | 1 | 11 | A | Ex. 1b | 3.0 | 180 |
| Ex. 2a | 2 | 9 | A | Ex. 2b | 5.4 | 195 |
| Ex. 3a | 3 | 7 | A | Ex. 3b | 5.4 | 238 |
| Ex. 4a | 4 | 7 | A | Ex. 4b | 5.4 | 238 |
| Ex. 5a | 5 | 11 | A | Ex. 5b | 5.4 | 323 |
| Ex. 6a | 6 | 12 | A | Ex. 6b | 6.0 | 275 |
| Ex. 7a | 7 | 17 | A | Ex. 7b | 4.8 | 226 |
| Ex. 8a | 8 | 14 | A | Ex. 8b | 4.8 | 170 |
| Ex. 9a | 9 | 13 | A | Ex. 9b | 4.8 | 187 |
| Ex. 10a | 10 | 46 | A | Ex. 10b | 4.8 | 121 |
| Ex. 11a | 11 | 31 | A | Ex. 11b | 3.0 | 107 |
| Comp. Ex. 1a | 1,6-hexanediol dimethacrylate | 8 | C | Comp. Ex. 1b | 6.0 | 531 |
| Comp. Ex. 2a | 1,3-butanediol dimethacrylate | 4 | C | Comp. Ex. 2b | 6.0 | 555 |
| Comp. Ex. 3a | Neopentyl glycol dimethacrylate | 8 | C | Comp. Ex. 3b | 7.8 | 391 |
| Comp. Ex. 4a | Diethylene glycol dimethacrylate | 5 | B | Comp. Ex. 4b | 12.0 | 409 |
| Comp. Ex. 5a | Polyethylene glycol dimethacrylate (p = 9) | 35 | A | Comp. Ex. 5b | 9.0 | 262 |
| Comp. Ex. 6a | Glycerol dimethacrylate | 23 | A | Comp. Ex. 6b | 4.5 | 230 |
| Comp. Ex. 7a | 1-(acryloyloxy)-3-(methacryloyloxy)-2-propanol | 29 | A | Comp. Ex. 7b | 4.8 | 230 |
| Comp. Ex. 8a | Comparative compound 1 | 34 | A | Comp. Ex. 8b | 4.8 | 208 |
| Comp Ex. 9a | Comparative compound 2 | 60 | A | Comp. Ex. 9b | 3.0 | 104 |
| Comp. Ex. 10a | Comparative compound 3 | 248 | A | Comp. Ex. 10b | 3.0 | 116 |

From Table 1, it can be seen that the photopolymerizable compounds of Examples 1a to 9a had a low viscosity and little odor. Further, it can be seen that the photocurable compositions of Examples 1b to 9b using the photopolymerizable compounds of Examples 1a to 9a were excellent in photopolymerizability and photo-curability. On the other hand, it can be seen that the photopolymerizable compounds of Examples 10a and 11a having a tertiary hydroxyl group in the molecules thereof had little odor and a very high photo-curability although their viscosity was a bit high.

Here, T1, which is the indicator of photopolymerizability, indicates a better photopolymerizability as the value is smaller, and is preferably 7 seconds or shorter, and more preferably 5 seconds or shorter. Meanwhile, the curing energy, which is the indicator of photo-curability, likewise indicates a better photo-curability as the value is smaller, and is preferably 350 mJ/cm$^2$ or less, and more preferably 250 mJ/cm$^2$ or less. The photopolymerizable compounds of the present invention achieved the effects described above because they had a plurality of polymerizable functional groups and a specific polar structure in a molecule thereof. Among them, photopolymerizable compounds having a group having an ester structure had little odor, were excellent in photopolymerizability and photo-curability, and had a particularly low viscosity, as can be seen.

As compared with this, it can be seen that although the photopolymerizable compounds of Comparative Examples 1a to 3a had a low viscosity, the photocurable compositions of Comparative Examples 1b to 3b using the same had the curing energy, which was the indicator of photo-curability, risen to a high value (i.e., required a lot of energy for curing). Further, these photopolymerizable compounds had no polar functional group on their mother nucleus structure, and was considered to have a higher volatility than the photopolymerizable compounds of Examples, which led to their unfavorable achievement in odor.

The photopolymerizable compounds of Comparative Examples 4a and 5a were bifunctional methacrylate compounds having an ethylene glycol chain on their mother nucleus structure. In this case, Comparative Example 4a having a shorter ethylene glycol chain had a lower viscosity, but the photocurable composition of Comparative Example 4b using the same had poor achievements in both of photopolymerizability and photo-curability. On the other hand, Comparative Example 5a having a longer ethylene glycol chain (p=9) had a bit higher viscosity, but the corresponding photocurable composition achieved a higher photo-curability owing to the influence of the higher molecular weight of the monomer. However, it can be seen that its photoreactivity was low (T1=9.0 s). This means that the reactive sites of the monomer tend to remain unchanged in the photo-curing process.

Further, the photopolymerizable compounds of Comparative Examples 6a and 7a into which a secondary hydroxyl group, which was a protic polar structure, was incorporated, and the photopolymerizable compound of Comparative Example 8a into which a urethane structure was incorporated had little odor, and the photocurable compositions of Comparative Examples 6b to 8b using the same achieved better photopolymerizability and photo-curability than the photocurable compositions of Comparative Examples 1b to 5b. However, it is hard to say that the better achievements in photopolymerizability and photo-curability were satisfactory, considering that the viscosity of the photopolymerizable compounds was a bit high.

Furthermore, the photocurable compositions of Comparative Examples 9b and 10b using the photopolymerizable compound of Comparative Example 9a into which a urethane structure, which was an aprotic polar structure, was incorporated, and the photopolymerizable compound of comparative Example 10a in which the ester structure was bonded reversely from Examples achieved better photopolymerizability and photo-curability, but their corresponding photopolymerizable compounds had a high viscosity that was higher than 50 mPa·s.

Examples 1c to 11c

<Production of Ink>

Each of the photopolymerizable compounds of Examples 1a to 11a (100 parts), a photopolymerization initiator IRGACURE 907 (manufactured by BASF Japan Ltd.) (10 parts), and a carbon black MICROLITH BLACK C-K (manufactured by BASF Japan Ltd.) (3 parts) were mixed, to thereby obtain inks of Examples 1c to 11c.

Examples 1d to 11d

Each of the photopolymerizable compounds of Examples 1a to 11a (100 parts), a photopolymerization initiator IRGACURE 907 (manufactured by BASF Japan Ltd.) (10 parts), and a blue pigment MICROLITH BLUE 4G-K (manufactured by BASF Japan Ltd.) (3 parts) were mixed, to thereby obtain inks of Examples 1d to 11d.

<Ink Evaluation 1>

The inks of Examples 1c to 11c and Examples 1d to 11d were each ink-jetted onto a glass slide, and then irradiated and cured with an ultraviolet ray having a wavelength of 365 nm at 200 mW/cm² with a UV irradiator LH6 (manufactured by Fusion Systems Japan Co., Ltd.). As a result, the inks could be ink-jetted without troubles, and the respective ink images cured sufficiently.

The inks substantially correspond to products composed of the photocurable compositions of Examples 1b to 11b. However, just to make sure, photopolymerizability and photo-curability of the inks were measured in the same manner as for the photocurable compositions. As a result, it was confirmed that the inks were excellent just the same as the photocurable compositions.

<Ink Evaluation 2>

The pen tip of a dip pen was dipped in the inks of Examples 1c to 11c and Examples 1d to 11d, and characters were written on a PET film and regular paper. After this, the written inks were irradiated and cured with an ultraviolet ray having a wavelength of 365 nm at 200 mW/cm² with a UV irradiator LH6 (manufactured by Fusion Systems Japan Co., Ltd.). As a result, the respective ink images cured sufficiently.

Aspects of the present invention are as follows, for example.

<1> An ink, including:

a compound represented by general formula (1) below,

[Chem. 34]

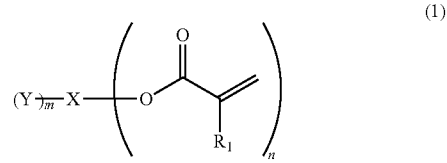

where in the formula above, $R_1$ represents a hydrogen atom or a methyl group, n represents an integer of 2 or greater, a plurality of $R_1$ may be the same as or different from each other, X represents a hydrocarbon group having 2 to 10 carbon atoms, Y represents a tertiary hydroxyl group, or a group having an ester structure, and m represents an integer of 1 or greater.

<2> The ink according to <1>, wherein Y in the general formula (1) is a group represented by general formula (2) below, or general formula (3) below, or both thereof,

[Chem. 35]

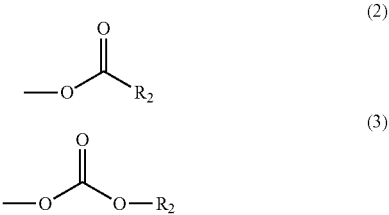

where in the formulae above, $R_2$ represents a hydrocarbon group having 1 to 15 carbon atoms.

<3> The ink according to <2>,
wherein $R_2$ in the general formula (2) or (3) is a group represented by general formula (4) below,

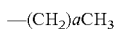 (4)

where in the formula above, a represents an integer of from 0 to 2.

<4> The ink according to any one of <1> to <3>,
wherein n in the compound represented by the general formula (1) is 2.

<5> The ink according to any one of <1> to <4>,
wherein in the compound represented by the general formula (1), n+m≤4.

<6> The ink according to any one of <1> to <5>,
wherein a viscosity of the compound represented by the general formula (1) at 25° C. is 20 mPa·s or lower.

<7> An ink cartridge, including:
the ink according to any one of <1> to <6> contained therein.

<8> An inkjet recording apparatus, including:
the ink cartridge according to <7> mounted thereon.

<9> A printed matter, including:
a print recorded with the ink according to any one of <1> to <6>.

<10> A photopolymerizable compound represented by general formula (1) below,

[Chem. 36]

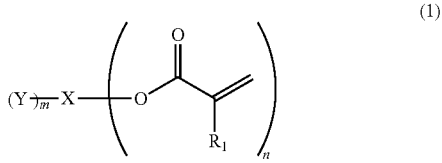 (1)

where in the formula above, $R_1$ represents a hydrogen atom or a methyl group, n represents an integer of 2 or greater, a plurality of $R_1$ may be the same as or different from each other, X represents a hydrocarbon group having 2 to 10 carbon atoms, Y represents a tertiary hydroxyl group, or a group having an ester structure, and m represents an integer of 1 or greater.

<11> The photopolymerizable compound according to <10>,
wherein Y in the general formula (1) is a group represented by general formula (2) below, or general formula (3) below, or both thereof,

[Chem. 37]

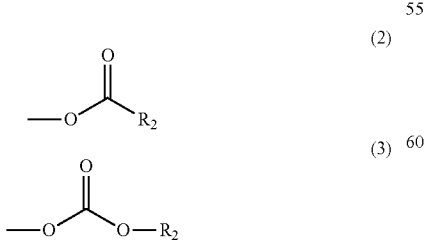

where in the formulae above, $R_2$ represents a hydrocarbon group having 1 to 15 carbon atoms.

<12> The photopolymerizable compound according to <11>,
wherein $R_2$ in the general formula (2) or (3) is a group represented by general formula (4) below,

 (4)

where in the formula above, a represents an integer of from 0 to 2.

<13> The photopolymerizable compound according to any one of <10> to <12>,
wherein n in the general formula (1) is 2.

<14> The photopolymerizable compound according to any one of <10> to <13>,
wherein in the general formula (1), n+m≤4.

<15> The photopolymerizable compound according to any one of <10> to <14>,
wherein a viscosity of the compound represented by the general formula (1) at 25° C. is 20 mPa·s or lower.

<16> A photocurable composition, including:
the photopolymerizable compound according to any one of <10> to <15>.

<17> A three-dimensional object formation material, including:
the photocurable composition according to <16>.

<18> A three-dimensional object produced by curing the three-dimensional object formation material according to <17>.

REFERENCE SIGNS LIST 10 ink cartridge
11 ink bag
12 ink injection port
13 ink discharge port
14 cartridge case
21 print target base material feeding roll
22 print target base material
23 printing unit
23a yellow printing unit
23b magenta printing unit
23c cyan printing unit
23d black printing unit
24a light source for photo-curing a yellow ink
24b light source for photo-curing a magenta ink
24c light source for photo-curing a cyan ink
24d light source for photo-curing a black ink
25 process unit
26 printed matter take-up roll

The invention claimed is:
1. An ink, comprising a compound represented by formula (1):

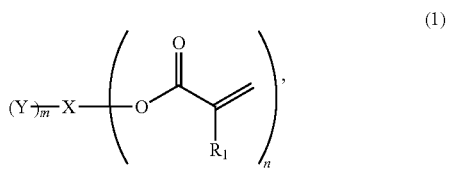 (1)

wherein:
$R_1$ represents a hydrogen atom or a methyl group,
n represents an integer of 2, such that a plurality of $R_1$ may be same as or different from each other,
X represents a hydrocarbon group having 2 to 10 carbon atoms, Y is an ester group represented by formula (2):

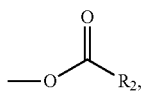  (2)

in which the ester group does not derive from a primary alcohol,
$R_2$ represents a hydrocarbon group having 1 to 15 carbon atoms, and
m represents an integer of 1 or greater.

2. The ink according to claim 1, wherein:
$R_2$ in the formula (2) is a group represented by formula (4):

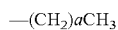  (4);

and a represents an integer of from 0 to 2.

3. The ink according to claim 1, wherein in the compound represented by the formula (1), n+m≤4.

4. The ink according to claim 1, wherein a viscosity of the compound represented by the formula (1) at 25° C. is 20 mPa·s or lower.

5. An ink cartridge, comprising:
an ink comprising a compound represented by formula (1):

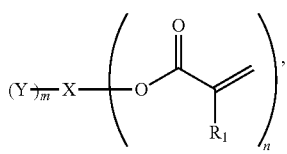  (1)

wherein:
$R_1$ represents a hydrogen atom or a methyl group;
n represents an integer of 2, such that a plurality of $R_1$ may be same as or different from each other;
X represents a hydrocarbon group having 2 to 10 carbon atoms;
Y is an ester group represented by formula (2):

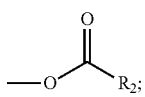  (2)

in which the ester group does not derive from a primary alcohol; and
$R_2$ represents a hydrocarbon group having 1 to 15 carbon atoms, and
m represents an integer of 1 or greater.

6. An inkjet recording apparatus, comprising the ink cartridge of claim 5 mounted thereon.

7. A printed matter, comprising a print recorded with the ink of claim 1.

8. A photopolymerizable compound represented by formula (1):

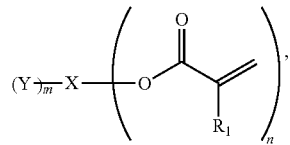  (1)

wherein:
$R_1$ represents a hydrogen atom or a methyl group,
n represents an integer of 2, such that a plurality of $R_1$ may be same as or different from each other,
X represents a hydrocarbon group having 2 to 10 carbon atoms,
Y is an ester group represented by formula (2):

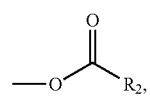  (2)

in which the ester group does not derive from a primary alcohol,
$R_2$ represents a hydrocarbon group having 1 to 15 carbon atoms, and
m represents an integer of 1 or greater.

9. The photopolymerizable compound according to claim 8, wherein
$R_2$ in the formula (2) is a group represented by formula (4):

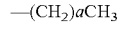  (4);

and a represents an integer of from 0 to 2.

10. The photopolymerizable compound according to claim 8, wherein in the general formula (1), n+m≤4.

11. The photopolymerizable compound according to claim 8, wherein a viscosity of the compound represented by the formula (1) at 25° C. is 20 mPa·s or lower.

12. A photocurable composition, comprising the photopolymerizable compound of claim 8.

13. A three-dimensional object formation material, comprising the photocurable composition of claim 12.

14. A three-dimensional object produced by curing the three-dimensional object formation material of claim 13.

15. The ink according to claim 1, wherein the ester group derives from a secondary alcohol or a tertiary alcohol.

16. The ink cartridge according to claim 5, wherein the ester group derives from a secondary alcohol or a tertiary alcohol.

17. The photopolymerizable compound according to claim 8, wherein the ester group derives from a secondary alcohol or a tertiary alcohol.

18. The ink according to claim 1, wherein the compound is represented by the following formula:

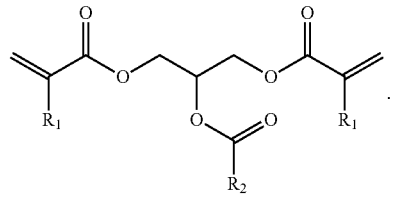

19. The ink cartridge according to claim 5, wherein the compound is represented by the following formula:
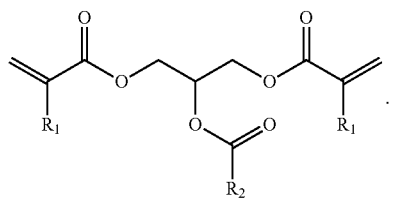
20. The photopolymerizable compound according to claim 8, wherein the compound is represented by the following formula:
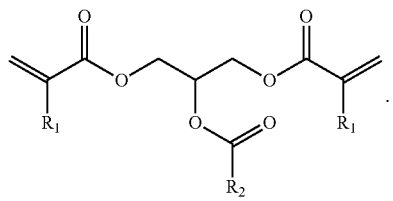
* * * * *